United States Patent
Brasile

(10) Patent No.: US 9,994,811 B2
(45) Date of Patent: Jun. 12, 2018

(54) REDUCING THE IMMUNOGENICITY OF ALLOGRAFTS

(71) Applicant: Lauren Brasile, Albany, NY (US)

(72) Inventor: Lauren Brasile, Albany, NY (US)

(*) Notice: Subject to any disclaimer, the term of this patent is extended or adjusted under 35 U.S.C. 154(b) by 0 days. days.

(21) Appl. No.: 14/879,637

(22) Filed: Oct. 9, 2015

(65) Prior Publication Data

US 2016/0160176 A1 Jun. 9, 2016

Related U.S. Application Data

(60) Provisional application No. 62/061,926, filed on Oct. 9, 2014.

(51) Int. Cl.
 *C12N 5/00* (2006.01)
 *A61K 35/15* (2015.01)
 *A01N 1/02* (2006.01)

(52) U.S. Cl.
 CPC .......... *C12N 5/0087* (2013.01); *A01N 1/0226* (2013.01); *A01N 1/0247* (2013.01); *A61K 35/15* (2013.01); *C12N 2501/51* (2013.01); *C12N 2501/52* (2013.01)

(58) Field of Classification Search
 CPC .............. C12N 5/0087; C12N 2501/51; C12N 2501/52; A61K 35/15; A01N 1/0226; A01N 1/0247
 See application file for complete search history.

(56) References Cited

U.S. PATENT DOCUMENTS

| | | |
|---|---|---|
| 5,599,659 A | 2/1997 | Brasile et al. |
| 5,643,712 A | 7/1997 | Brasile |
| 5,699,793 A | 12/1997 | Brasile |
| 5,702,881 A | 12/1997 | Brasile et al. |
| 5,843,024 A | 12/1998 | Brasile |
| 6,024,698 A | 2/2000 | Brasile |
| 6,375,613 B1 | 4/2002 | Brasile |
| 6,582,953 B2 | 6/2003 | Brasile |
| 6,642,045 B1 | 11/2003 | Brasile |
| 7,985,536 B2 | 7/2011 | Brasile |
| 8,748,164 B2 | 6/2014 | Brasile |
| 9,232,784 B2 | 1/2016 | Brasile |
| 2010/0028848 A1* | 2/2010 | Parker .................. C12N 15/111 435/1.1 |

OTHER PUBLICATIONS

Stone et al. Mechanical removalofdendriticcell-generating nonclassical monocytesviaexvivolungperfusion. The Journal of Heart and Lung Transplantation. vol. 33, Issue 8, Aug. 2014, pp. 864-869.*
Cypel et al. Normothermic Ex Vivo Perfusion Prevents Lung Injury Compared to Extended Cold Preservation for Transplantation. American Journal of Transplantation 2009; 9: 2262-2269.*

* cited by examiner

*Primary Examiner* — Taeyoon Kim
(74) *Attorney, Agent, or Firm* — Heslin Rothenberg Farley & Mesiti P.C.; Kathy Smith Dias, Esq.

(57) ABSTRACT

There is provided an ex vivo method for reducing the immunogenicity of a tissue or organ prior to transplantation, comprising:
 (a) establishing the tissue or organ in a warm perfusion system capable of supporting oxidative metabolism of the tissue or organ;
 (b) perfusing the tissue or organ with a warm non-blood perfusion solution for at least 1 hour to allow passenger leukocytes within the tissue or organ to migrate from the tissue or organ into the recirculating perfusion solution;
 (c) isolating the passenger leukocytes from the recirculating perfusion solution to prevent the passenger leukocytes from re-entering the tissue or organ.

7 Claims, 6 Drawing Sheets
(4 of 6 Drawing Sheet(s) Filed in Color)

REDUCING THE IMMUNOGENICITY OF ALLOGRAFTS

CROSS-REFERENCE TO RELATED APPLICATIONS

This application claims the priority of U.S. provisional application 62/061,926 filed on Oct. 9, 2014, the contents of which are hereby incorporated herein by reference in their entirety.

TECHNICAL FIELD

The present invention relates to methods for reducing the immunogenicity or preventing immune rejection of tissues or organs prior to transplantation, methods for obtaining passenger leukocytes from donor tissues or organs and for reducing their immunogenicity, as well as the use of these passenger leukocytes for reducing the immunogenicity or preventing immune rejection of the donor tissue or organs in recipient patients.

BACKGROUND OF THE INVENTION

Organ and tissue transplantation is a unique immunologic situation because both donor and recipient antigen presenting cells (APCs) are present at the time of reperfusion. The donor APCs are immune cells that become trapped within an allograft at the time of organ retrieval as part of normal immune surveillance. The donor APCs are referred to as passenger leukocytes. The passenger leukocytes migrate out of the allograft within hours of re-implantation and traffic to the secondary lymphoid tissues of the patient where they serve as MHC class II positive APCs stimulating direct activation of recipient naive CD4+ T cells (known as the direct pathway of allorecognition). The ability of passenger leukocytes to activate recipient T cells can be attributed in part to the expression of costimulatory molecules on the cell surface of the passenger leukocytes that interact with receptor ligands on the surface of T cells. Key co-stimulatory molecules found on the surface of passenger leukocytes include the CD80 and CD86 proteins which provide a co-stimulatory signal to the CD28 T cell receptor; and the CD40 protein which provides a co-stimulatory signal to the CD154 T cell receptor. Once activated, the patient's T cells clonally expand and traffic to the donor transplant site leading to acute transplant rejection. Direct antigen presentation by the passenger leukocytes is most potent during the first week post-transplantation. Direct T cell priming is time limited because the passenger leukocytes are eventually destroyed.

Much work has focused on preventing T cell activation following transplantation by attempting costimulatory blockade within the recipient patient. Current therapies focus on using immunosuppressive regimens that impact the effector arm of the recipient's immune system (eg. by preventing activation and proliferation of naïve CD4+ T cells following interaction with the donor passenger leukocytes, and blocking their infiltration into the allograft). However, when costimulatory blockade has been attempted in vivo, toxicity is a complicating issue. For example, whilst monoclonal antibodies targeting CD28, CD40 and CD40L have great potential to ameliorate allograft rejection, these therapies have been associated with severe complications when administered systemically. The side-effects have included cytokine storm, disseminated intravascular coagulation and thrombotic complications that have led to significant morbidity and mortality. An additional complication of systemic administration of monoclonal antibodies is the suppression of viral immune responses that can result in severe systemic manifestations. An approach postulated to enhance the efficacy of costimulatory blockade entails combining treatments to address several costimulatory pathways simultaneously. Such a combined approach could provide better efficacy to address the redundancy existing in T cell costimulatory pathways. However, given the potential risks associated with in vivo administration of a single therapeutic to blockade a single pathway, blockade of multiple pathways may present significant increased risks of complications.

Current therapies for preventing transplant rejection therefore focus entirely on targeting the recipient's immune system, rather than attempting to prevent antigen presentation by targeting the passenger leukocytes themselves. Indeed, current immunosuppressive drugs do not appreciably alter the migration of the donor passenger leukocytes out of an allograft and into the secondary lymphatics of the recipient, nor do they ameliorate the immune response initiated by the passenger leukocytes in the recipient's secondary lymphatics.

If direct antigen presentation mediated by passenger leukocytes can be prevented during the early posttransplant period, allosensitization leading to acute rejection may be prevented. Furthermore, if a population of passenger leukocytes can survive within the patient without inducing antigen presentation, a state of immune tolerance may be induced. Indeed, survival of even rare populations of passenger leukocytes could result in a tolerate state. The dissemination of the donor passenger leukocytes entails migration to the secondary lymphatics for a period of approximately 14 days after which they migrate into other tissues in the recipient. The survival of even a rare population of the donor passenger leukocytes has been postulated to be the basis of micro-chimerism that is associated with a tolerant state.

So far, only modest efforts have been made to focus on treating the allograft itself, prior to transplantation. Attempts to date to remove passenger leukocytes from human organs have not been successful.

There is therefore a need in the art for new ways of targeting the passenger leukocyte population in donor tissues and organs to prevent allorecognition and transplant rejection.

SUMMARY OF THE INVENTION

The present invention provides an ex vivo method for reducing the immunogenicity of a tissue or organ prior to transplantation, comprising:
(a) establishing the tissue or organ in a warm perfusion system capable of supporting oxidative metabolism of the tissue or organ;
(b) perfusing the tissue or organ with a warm non-blood perfusion solution for at least 1 hour to allow passenger leukocytes within the tissue or organ to migrate from the tissue or organ into the recirculating perfusion solution;
(c) isolating passenger leukocytes from the recirculating perfusion solution to prevent the passenger leukocytes from re-entering the tissue or organ.

The method of the present invention efficiently reduces the immunogenicity of donor tissues or organs by removing passenger leukocytes from within the tissues or organs prior to transplantation and preventing their re-entry into the tissue or organ by removing them from the re-circulating perfusion solution. Passenger leukocytes trapped within donor tissues or organs are known to promote allosensitization of the recipient patient to antigens located within the donor tissue or organ by activating T cells within the recipient patient that recognise these non-self antigens. Activation of T cell response within the recipient leads to a targeted immune response against the transplanted tissue or organ and acute rejection of the transplant. By removing the passenger leukocytes from the tissue or organ prior to transplantation, antigen presentation by passenger leukocytes is prevented, thereby avoiding activation of T cells within the patient. The present inventor has demonstrated that passenger leukocytes can be efficiently removed from donor tissue or organ by maintaining the tissue or organ within a warm perfusion system under conditions that support a near normal metabolic state. Under such conditions, passenger leukocytes trapped within the tissue or organ migrate from the tissue or organ into the recirculating perfusion solution of the system, where they can be collected and removed. The migration of leukocytes in the warm perfusion system mimics the in vivo situation in which passenger leukocytes migrate from the transplanted tissue or organ into the patient. The migration of passenger leukocytes out of donor tissues or organs requires significant amounts of ATP and the bio-energetic demands increase dramatically upon cellular activation events. In particular, the inventor has found that the metabolic rate during ex vivo perfusion controls the energy that is available to the donor passenger leukocytes and the temperature likewise directly impacts metabolism. The use of a warm perfusion system is therefore essential for ensuring that the passenger leukocytes migrate out of the donor tissue or organ. The effects of temperature on passenger leukocyte migration are demonstrated by Examples 1-3. In this regard, Example 1 demonstrates that the number of donor passenger leukocytes present within isolated donor kidneys is significantly reduced following 24 hours of ex vivo warm perfusion (see FIGS. 1 and 2 and Table 3). Example 2 demonstrates that the amount of passenger leukocytes removed from the tissue or organ increases in a time dependent manner (see Table 3). Example 3 further demonstrates that in order to achieve maximum migration of donor passenger leukocytes from the tissue or organ, the tissue or organ must be perfused under warm perfusion conditions (see FIG. 3). When perfusion is performed under hypothermic conditions, the majority of the donor passenger leukocytes remain trapped within the tissue or organ, as they lack the required energy resources to undergo migration from the tissue or organ to the recirculating perfusion solution.

The present invention also provides an ex vivo method for reducing the immunogenicity of a tissue or organ prior to transplantation, comprising:
(a) establishing the tissue or organ in a warm perfusion system capable of supporting oxidative metabolism of the tissue or organ;
(b) perfusing the tissue or organ with a warm non-blood perfusion solution for at least 1 hour to allow passenger leukocytes within the tissue or organ to migrate from the tissue or organ into the recirculating perfusion solution;
(c) isolating passenger leukocytes from the recirculating perfusion solution to prevent the passenger leukocytes from re-entering the tissue or organ;
(d) treating the isolated passenger leukocytes with an agent that reduces or inhibits the expression or activity of at least one protein on the surface of the passenger leukocyte that co-stimulates T cell activation; and
(e) re-introducing the treated passenger leukocytes into the perfusion solution and perfusing the tissue or organ for a time sufficient for the treated leukocytes to enter the tissue or organ.

The inventor has also observed that the immunogenicity of donor tissues and organs can be further reduced by treating the passenger leukocytes isolated from the donor tissue or organ with an agent that blocks their ability to co-stimulate and activate T cells (by blocking the expression or activity of co-stimulatory molecules present on the passenger leukocyte surface) and re-introducing the treated passenger leukocytes into the tissue or organ prior to transplantation whilst the tissue or organ is undergoing warm perfusion. Once the donor tissue or organ is transplanted into the recipient patient, the treated passenger leukocytes migrate from the donor tissue or organ into the patient. As a result of the treatment process, the treated passenger leukocytes are unable to deliver a co-stimulatory signal that activates T cells within the patient. This prevents activation of the direct pathway of allostimulation, helping to avoid acute transplant rejection. Furthermore, T cells that recognise donor antigen presented by the passenger leukocytes, but which do not receive a co-stimulatory signal, enter a state of anergy and become non-responsive to those antigens. This state of T cell anergy may induce immune tolerance in the patient to the donor antigens present on the donor tissue or organ.

Example 4 demonstrates that treatment of the recovered passenger leukocytes with antibodies that inhibit the activity of their co-stimulatory molecules (ie. CD40, CD80 and CD86) blocks their ability to stimulate proliferation of mononuclear cells (see FIG. 4).

The treated donor leukocytes thus reduce the immunogenicity of the donor tissue or organ by inducing immune tolerance in the patient to the donor tissue or organ. The treated donor leukocytes reduce the immunogenicity of the donor tissue or organ by preventing stimulation of the direct pathway of allorecognition in the patient. The treated donor leukocytes reduce the immunogenicity of the donor tissue or organ by inducing a state of anergy in the donor-specific T cells of the patient.

A key advantage of the method of the present invention is that the donor leukocytes can be treated ex vivo to achieve efficient co-stimulatory blockade. This avoids the need to administer the co-stimulatory blocking agents directly to the recipient patient, and therefore presents the opportunity to achieve high dose, multi-drug costimulatory blockade without the risks associated with systemic administration of therapeutics. The ex vivo method permits the removal of non-incorporated agents by flushing the treated tissue or organ prior to re-implantation, further reducing the risk of side effects. This method also presents the opportunity to increase efficacy by using multiple therapeutics.

The present invention provides a method for reducing the immunogenicity of a donor tissue or organ, comprising:
(a) establishing the tissue or organ in an ex vivo warm perfusion system capable of supporting oxidative metabolism of the tissue or organ;
(b) perfusing the tissue or organ with a warm non-blood perfusion solution for at least 1 hour to allow donor passenger leukocytes within the tissue or organ to migrate from the tissue or organ into the recirculating perfusion solution;
(c) isolating donor passenger leukocytes from the recirculating perfusion solution to prevent the donor passenger leukocytes from re-entering the tissue or organ.

(d) treating the isolated donor passenger leukocytes with an agent that reduces or inhibits the expression or activity of at least one protein on the surface of the donor passenger leukocyte that co-stimulates T cell activation; and (e) administering the treated donor passenger leukocytes to the recipient patient prior to, during and/or after transplantation of the donor tissue or organ.

The method of the invention therefore allows the treated passenger leukocytes to be administered directly to the recipient patient. This increases the flexibility of the method by allowing the patient to be administered with the treated passenger leukocytes prior to, during and/or after transplantation of the donor tissue or organ.

The treated passenger leukocytes administered directly to the patient are able to reduce the immunogenicity of the donor tissue or organ by inducing immune tolerance in the patient to the donor tissue or organ. The treated passenger leukocytes may reduce the immunogenicity of the donor tissue or organ by preventing stimulation of the direct pathway of allorecognition in the patient. The treated passenger leukocytes may reduce the immunogenicity of the donor tissue or organ by inducing a state of anergy in the donor-specific T cells of the patient.

In one embodiment, the treated passenger leukocytes are administered systemically to the recipient patient prior to, during and/or after transplantation of the donor tissue or organ. Advantageously, administration of the treated passenger leukocytes prior to transplantation enables the recipient patient to develop an immune tolerance to the donor tissue or organ prior to transplantation.

In one embodiment, the treated passenger leukocytes are administered directly into the transplanted tissue or organ during the transplantation procedure or after transplantation has taken place.

In one embodiment, the treated passenger leukocytes are administered directly to donor tissue or organ prior to transplantation, whilst the tissue or organ is being perfused in a warm perfusion system.

The present invention also provides an ex vivo method for reducing the immunogenicity of a tissue or organ prior to transplantation, comprising: (a) establishing the tissue or organ in a warm perfusion system capable of supporting oxidative metabolism of the tissue or organ; and (b) perfusing the tissue or organ for at least 1 hour with a warm non-blood perfusion solution comprising an agent that reduces or inhibits the expression or activity of at least one protein on the surface of passenger leukocytes that co-stimulates T cell activation.

Advantageously, this method allows the passenger leukocytes to be treated without having to first isolate the leukocytes from the donor tissue or organ. This method therefore provides a simplified way of reducing the immunogenicity of a tissue or organ prior to transplantation. Example 5 demonstrates that the passenger leukocytes present within a donor kidney can be treated in situ in the warm perfusion system using an antagonistic anti-CD86 antibody. An additional advantage of treating the tissue or organ in situ in the warm perfusion system is that other antigen-presenting cells present within the tissue or organ (eg. vascular endothelial cells) are also exposed to the agent, thereby achieving co-stimulatory blockage of all antigen-presenting cells located within the tissue or organ.

The present invention provides a method for preventing immune rejection of a donor tissue or organ in a recipient patient comprising: administering the recipient patient with donor passenger leukocytes prior to, during and/or after transplantation of the donor tissue organ into the patient; wherein the passenger leukocytes are obtained from the donor tissue or organ prior to transplantation using an ex vivo perfusion method as described herein, and have been treated with an agent that reduces or inhibits the expression or activity of at least one protein on the surface of the donor passenger leukocytes that co-stimulates T cell activation.

The present invention also provides passenger leukocytes for use in a method of preventing immune rejection of a donor tissue or organ in a recipient patient, wherein the passenger leukocytes are obtained from the donor tissue or organ prior to transplantation using an ex vivo perfusion method as described herein; and treated with an agent that reduces or inhibits the expression or activity of at least one protein on the surface of the donor passenger leukocyte that co-stimulates T cell activation.

The inventor has found that immune rejection of donor tissues or organs transplanted into recipient patients can be prevented by administering treated passenger leukocytes obtained from the donor tissue or organ to the recipient patient. As described herein, the passenger leukocytes are treated so as to blockade their co-stimulatory signal, preventing them from activating T cells within the recipient patient. The treated passenger leukocytes thus prevent immune rejection of the donor tissue or organ by inducing immune tolerance in the patient to the donor tissue or organ. The treated passenger leukocytes prevent immune rejection of the donor tissue or organ by preventing stimulation of the direct pathway of allorecognition in the patient. The treated passenger leukocytes prevent immune rejection of the donor tissue or organ by inducing a state of anergy in the donor-specific T cells of the patient.

The treated passenger leukocytes can be administered directly to the recipient patient, prior to, during and/or after transplantation of the donor tissue or organ.

In one embodiment, the treated passenger leukocytes are administered systemically to the recipient patient prior to, during and/or after transplantation of the donor tissue or organ. Advantageously, administration of the treated passenger leukocytes prior to transplantation enables the recipient patient to develop an immune tolerance to the donor tissue or organ prior to transplantation.

In one embodiment, the treated passenger leukocytes are administered directly into the transplanted tissue or organ during the transplantation procedure or after transplantation has taken place.

In one embodiment, the treated passenger leukocytes are administered directly to donor tissue or organ prior to transplantation, whilst the tissue or organ is being perfused in a warm perfusion system.

The present invention provides an ex vivo method for obtaining passenger leukocytes from a tissue or organ; comprising:

(a) establishing the tissue or organ in a warm perfusion system capable of supporting oxidative metabolism of the tissue or organ;

(b) perfusing the tissue or organ with a warm non-blood perfusion solution for at least 1 hour to allow passenger leukocytes within the tissue or organ to migrate from the tissue or organ into the recirculating perfusion solution; and (c) isolating the passenger leukocytes from the recirculating perfusion solution.

This method provides a convenient way of collecting donor passenger leukocytes from tissues or organs for further use in methods of reducing the immunogenicity of the tissue or organ in a recipient patient, or for use in methods of preventing immune rejection of the tissue or organ in a recipient patient.

The present invention provides an ex vivo method for reducing the immunogenicity of passenger leukocytes, comprising:
(a) obtaining passenger leukocytes from a tissue or organ using the ex vivo method described herein; and
(b) treating the isolated passenger leukocytes with an agent that reduces or inhibits the expression or activity of at least one protein on the surface of the passenger leukocytes that co-stimulates T cell activation.

The present invention provides the use of passenger leukocytes for reducing the immunogenicity of a donor tissue or organ in a recipient patient; wherein the passenger leukocytes are obtained from the donor tissue or organ prior to transplantation using an ex vivo perfusion method as described herein; and are treated with an agent that reduces or inhibits the expression or activity of at least one protein that co-stimulates T cell activation.

The inventor has found that passenger leukocytes obtained from donor tissues or organs can be used to reduce the immunogenicity of the donor tissues or organs when they are transplanted into recipient patients. As described herein, the passenger leukocytes are treated so as to blockade their co-stimulatory signal, preventing them from activating T cells within the recipient patient.

Advantageously, the treated passenger leukocytes can be used to reduce the immunogenicity of donor tissues or organs by inducing immune tolerance in the patient to the donor tissue or organ. The treated passenger leukocytes can be used to reduce the immunogenicity of donor tissues or organs by preventing stimulation of the direct pathway of allorecognition in the patient. The treated passenger leukocytes can be used to reduce the immunogenicity of the donor tissue or organ by inducing a state of anergy in the donor-specific T cells of the patient.

In one embodiment, the passenger leukocytes that are used to reduce the immunogenicity of donor tissues or organs can be administered directly to the recipient patient, prior to, during and/or after transplantation of the donor tissue or organ.

In one embodiment, the treated passenger leukocytes are administered systemically to the recipient patient prior to, during and/or after transplantation of the donor tissue or organ. Advantageously, administration of the treated passenger leukocytes prior to transplantation enables the recipient patient to develop an immune tolerance to the donor tissue or organ prior to transplantation.

In one embodiment, the treated passenger leukocytes are administered directly into the transplanted tissue or organ during the transplantation procedure or after transplantation has taken place.

In one embodiment, the treated passenger leukocytes are administered directly to donor tissue or organ prior to transplantation, whilst the tissue or organ is being perfused in a warm perfusion system.

The present invention provides the use of passenger leukocytes for preventing immune rejection of a donor tissue or organ in a recipient patient; wherein the passenger leukocytes are obtained from the donor tissue or organ prior to transplantation using an ex vivo perfusion method as described herein; and are treated with an agent that reduces or inhibits the expression or activity of at least one protein that co-stimulates T cell activation.

The inventor has found that passenger leukocytes obtained from donor tissues or organs can be used to prevent immune rejection of the donor tissues or organs when they are transplanted into recipient patients. As described herein, the passenger leukocytes are treated so as to blockade their co-stimulatory signal, preventing them from activating T cells within the recipient patient.

Advantageously, the treated passenger leukocytes can be used to prevent immune rejection of donor tissues or organs by inducing immune tolerance in the patient to the donor tissue or organ. The treated passenger leukocytes can be used to prevent immune rejection of donor tissues or organs by preventing stimulation of the direct pathway of allorecognition in the patient. The treated passenger leukocytes can be used to prevent immune rejection of the donor tissue or organ by inducing a state of anergy in the donor-specific T cells of the patient.

The passenger leukocytes that are used to prevent immune rejection of donor tissues or organs can be administered directly to the recipient patient, prior to, during and/or after transplantation of the donor tissue or organ.

In one embodiment, the treated passenger leukocytes are administered systemically to the recipient patient prior to, during and/or after transplantation of the donor tissue or organ. Advantageously, administration of the treated passenger leukocytes prior to transplantation enables the recipient patient to develop an immune tolerance to the donor tissue or organ prior to transplantation.

In one embodiment, the treated passenger leukocytes are administered directly into the transplanted tissue or organ during the transplantation procedure or after transplantation has taken place.

In one embodiment, the treated passenger leukocytes are administered directly to donor tissue or organ prior to transplantation, whilst the tissue or organ is being perfused in a warm perfusion system.

The terms used to describe the methods and uses of the present invention are as defined below.

As used herein, the term "ex vivo" means that the method is performed outside of the human or animal body.

As used herein, the term "tissue" means a collection of cells characterised by their ability to perform a particular physiologic function; and the term "organ" means a collection of tissues characterised by their ability to perform a particular physiologic function. The "organ" may be a kidney, heart, liver, lung, small bowel, pancreas, brain, eye, skin, limb or anatomic quadrant. In one embodiment, the organ is a kidney.

As used herein, the terms "passenger leukocytes" or "donor passenger leukocytes" are used to refer to the Major Histocompatibility Complex Class II positive leukocytes that become trapped within tissue or organ allografts at the time of organ procurement. These leukocytes are able to migrate out of the donor tissue or organ following transplantation into the recipient patient, and are responsible for sensitising the recipient's alloreactive T-lymphocytes, leading to acute transplant rejection. Passenger leukocytes found within donor tissues and organs include the professional antigen-presenting cells: dendritic cells, monocytes, macrophages and a subpopulation of B cells.

As used herein, the term "perfusion system" refers to the system that provides exsanguinous metabolic support (EMS) for a tissue or organ, such as that described in the International application WO 2004/105484. The perfusion system is responsible for maintaining and controlling the physiological processes of the tissue or organ. The perfusion system delivers a warm non-blood perfusion solution containing all the constituents necessary to re-establish, where necessary, and support oxidative metabolism by the tissue or organ.

The perfusion system may also reprocess the perfusion solution to ensure a continuous supply of nutrients and chemical energy substrates and remove metabolic by-products. Additionally, the perfusion system may monitor and control various parameters of the perfusion including temperature, vascular pressures, perfusion flow rate, OsM, pH, $PaO_2$, $PaCO_2$, nutrient delivery and the removal of waste products.

A schematic showing the basic components of a perfusion system is shown in FIG. 6.

Before a tissue or organ can be established in a perfusion system, the tissue or organ must be isolated from the rest of the physiologic system by removing or interrupting the arterial source of blood feeding the desired tissue or organ. Likewise, the venous outflow from the organ or section of anatomy is interrupted and the venous effluent is collected. If the tissue is completely excised from the body, then the enervation and lymphatics of the tissue are also isolated.

When establishing the tissue or organ in a warm perfusion system capable of supporting oxidative metabolism of the tissue or organ, the tissue or organ is flushed with a cell-free, buffered physiological solution at a temperature of about 25° C. to 37° C. to remove blood and blood products from the organ or tissue. The flushing may be done through the arterial system of the organ or tissue. The solution used to flush the tissue or organ may be the perfusion solution as described herein. It will be appreciated by those skilled in the art that the amount of the perfusion solution sufficient for use in flushing the organ may depend on the particular organ type and size, as well as the length of time the organ was deprived of blood flow. For example, 200 to 600 mls of the perfusion solution may be sufficient to flush a human kidney which has been deprived of blood flow for a period of 1-3 hours. In this way, any ischemic blood and acidotic products which have accumulated in the vascular space are removed. Further, pH is restored and fresh substrate is delivered to support anaerobic metabolism and other cellular pathways necessary for cellular integrity and function.

The step of establishing the tissue or organ in a warm perfusion system capable of supporting oxidative metabolism of the tissue or organ may be performed at a temperature of between about 25° C. and 37° C. Alternatively, this step may be performed at a temperature between about 25° C. and 35° C. Alternatively, this step may be performed at a temperature between about 30° C. and 34° C. Alternatively, this step may be performed at a temperature of about 32° C.

After flushing, the tissue or organ is immobilised in the perfusion system and connected to the perfusion solution path. The organ is then perfused with a warm non-blood perfusion solution, while various parameters of the perfusion are monitored by the system and regulated as necessary to maintain adequate metabolism of the organ or tissue. Organ function is also monitored, for example, by collecting an organ product, such as urine or bile, and evaluating whether physical and chemical parameters of the organ product are within the range associated with normal function for that particular organ.

The step of perfusing the tissue or organ with a warm non-blood perfusion solution may be performed a temperature of between about 25° C. and 37° C. Alternatively, this step may be performed at a temperature between about 25° C. and 35° C. Alternatively, this step may be performed at a temperature between about 30° C. and 34° C. Alternatively, this step may be performed at a temperature of about 32° C.

The step of perfusing the tissue or organ with a warm non-blood perfusion solution may be performed for at least 1 hour. Alternatively, the perfusion step may be performed for at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 hours. In one embodiment, the step of perfusing the tissue or organ with a warm non-blood perfusion solution is performed for at least 24 hours.

The step of perfusing the tissue or organ with a warm non-blood perfusion solution may be performed for up to 36, 48, 72, 96, 120, 144, 168, 192, 216, and 240 hours. In one embodiment, the perfusion step is performed for up to 72 hours. By increasing the duration of the warm perfusion step, more passenger leukocytes migrate out of the tissue or organ into the recirculating perfusion solution.

In one aspect of the invention, the tissue or organ is perfused for at least 1 hour with a warm non-blood perfusion solution comprising an agent that blocks the co-stimulatory activity of the passenger leukocytes (such as an agent that reduces or inhibits the expression or activity of at least one protein on the surface of passenger leukocytes that co-stimulates T cell activation). The perfusion step may be performed at a temperature of between about 25° C. and 37° C. Alternatively, this step may be performed at a temperature between about 25° C. and 35° C. Alternatively, this step may be performed at a temperature between about 30° C. and 34° C. Alternatively, this step may be performed at a temperature of about 32° C. The perfusion step may be performed for at least 1 hour. Alternatively, the perfusion step may be performed for at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 hours. In one embodiment, the step of perfusing is performed for at least 24 hours. The perfusion step may be performed for up to 36, 48, 72, 96, 120, 144, 168, 192, 216, and 240 hours. In one embodiment, the perfusion step is performed for up to 72 hours. By increasing the duration of the warm perfusion step, more passenger leukocytes migrate out of the tissue or organ into the recirculating perfusion solution.

The perfusion solution is perfused at a systolic pressure appropriate for the tissue or organ being maintained until a flow rate is achieved which is near normal for that particular organ or tissue. The skilled person will be familiar with organ specific flow requirements, as described in WO 2004/105484. By way of illustration but not limitation, a human kidney may be perfused with the solution at a systolic pressure of <80 mmHg with a flow rate>80 cc/min. The pH is maintained in a physiologic range by the injection of $CO_2$ or $O_2$ via an oxygenator. Delivery of oxygen to the organ may be facilitated by including an oxygen carrier as a component of the perfusion solution.

When the organ is a liver, two perfusion pathways are needed to account for the flow of the perfusion solution in the hepatic artery which entails a high pressure and low vascular flow; and to account for the flow of the perfusion solution in the portal vein which entails a low pressure and high flow.

As used herein, the term "supporting oxidative metabolism" means that the warm perfusion system provides the necessary conditions (eg. pH, oxygenation, temperature, osmolarity and nutrients) allowing the tissue or organ to be metabolically active and to generate ATP using oxidative metabolism.

The perfusion system supports oxidative metabolism in the tissue or organ at a sufficient level to support the ongoing function of the tissue or organ during the time it is isolated from the body or the circulatory system.

The perfusion system supports oxidative metabolism in the tissue or organ at a sufficient level to provide adequate metabolites and nutrients to maintain the tissue integrity with tight cellular functions and normal membrane polarity. The oxidative metabolism taking place therefore maintains cellular integrity of the tissue or organ.

The perfusion system supports oxidative metabolism in the tissue or organ at a sufficient level to ensure that the tissue or organ is maintained in a metabolically active state prior to transplantation.

A sufficient level of oxidative metabolism may be indicated by determining whether the tissue or organ is able to produce its functional product or possesses functional characteristics that are typical of the tissue or organ.

The warm perfusion system supports near normal oxidative metabolism in the tissue or organ. As a result the tissue or organ may be maintained at a near normal level of metabolism. As used herein, the terms "near normal oxidative metabolism" and "near normal metabolic rate" are defined as about 70-100% of the normal rate of metabolism for a particular organ as determined by measuring and evaluating whether functional characteristics of an organ are within the range associated with normal function for that particular organ. As used herein, the term "organ product" refers to any substance generated as the result of the secretory functions of an organ, frequently a fluid eg. bile from liver, urine from kidneys. It also includes mechanical functions such as kidney filtration or heart pumping.

Examples of functional characteristics include, but are not limited to, electrical activity in a heart as measured by electrocardiogram; physical and chemical parameters of organ product, for example, oxygen consumption and glucose utilization which can be ascertained from the change in the concentrations of oxygen and glucose in the perfusate during the perfusion period; pancreatic enzymes; heart enzymes; creatinine clearance and filtration functions of the kidneys, specific gravity of urine and the like. A detailed description of these functional tests can be found in U.S. Pat. No. 5,699,793.

In one embodiment, wherein the organ intended for transplantation is a kidney, functional characteristics can be assessed by measuring parameters including at least one parameter selected from: urine concentration of protein, urine concentration of glucose, urine concentration of creatinine, urine pH, urine osmolality, urine specific gravity, kidney vascular flow rate, oxygen consumption, and glucose utilization (as measured from the perfusate).

In one embodiment, wherein the organ intended for transplantation is a liver, functional characteristics can be assessed by measuring parameters including at least one parameter selected from: bile concentration of bile salts, bile concentration of cholesterol, bile concentration of alkaline phosphatase, bile pH, liver vascular flow rate, liver oxygen consumption, and liver glucose utilization (as measured from the perfusate).

In one embodiment, wherein the organ intended for transplantation is a pancreas, functional characteristics can be assessed by measuring parameters in including at least one parameter selected from: pancreatic amylase concentration, pancreatic lipase concentration, the hormone insulin, pancreatic secretion pH, pancreatic sodium levels, pancreatic potassium levels, and pancreas vascular flow rate, pancreatic oxygen consumption, and pancreatic glucose utilization (as measured from the perfusate).

In one embodiment, wherein the organ intended for transplantation is a heart, functional characteristics can be assessed by measuring parameters including, at least one parameter selected from: levels of heart enzymes (such as transaminases (aspartate aminotransferase, AST), lactate dehydrogenase (LD), fructose 1,6-diphosphate aldolase (ALS), malate dehydrogenase (MD), glutathione reductase (GR), creatine phosphokinase (CPK), hydroxybutyrate dehydrogenase (HBD)), heart vascular flow rate, heart oxygen consumption, and heart glucose utilization (as measured from the perfusate). Other parameters include measuring the heart electric potential by electrocardiogram (ECG).

In one embodiment, wherein the organ intended for transplantation is a small bowel, functional characteristics can be assessed by measuring parameters including at least one parameter selected from: functional assays such as gastric acid stimulation tests, absorption assays using tracer molecules, small bowel vascular flow rate, small bowel oxygen consumption, and small bowel glucose utilization (as measured from the perfusate).

As used herein, the term "perfusion solution" or "perfusate" means a non-blood buffered physiologic solution that supports oxidative metabolism of a tissue or organ, such as that described in the International application WO 2004/105484. In particular, the perfusion solution enables an organ or tissue to be maintained at a near normal rate of metabolism.

As used herein, the term "non-blood" excludes perfusates comprising substantially whole blood or its individual components. The perfusion solution used in the present invention may, however, contain a minimal amount of whole blood or a blood component, for example, red blood cells, serum or plasma. In one embodiment, the "non-blood perfusion solution" used in the perfusion system does not contain any amount of whole blood or blood component.

The perfusion solution used in the methods and uses of the invention comprises a base solution in the form of a buffered basal medium for maintaining pH at physiologic levels. In one embodiment, the buffered basal medium maintains the perfusion solution at a pH of 7.0 to 7.6. In one embodiment, the base solution maintains the perfusion solution at a pH of 7.30-7.45. The buffered basal medium may comprise essential and non-essential amino acids, carbohydrates, metabolites, inorganic ions, serum proteins, nitrogen bases, vitamins, a reducing agent and a buffering system. The buffered basal medium may be any commercially available salt solution or cell culture medium, (e.g., Hank's BSS, Earle's BSS, Ham's F12, DMEN, Iscove's MEM, M199, RPMI 1640, RSM-210.) The buffered basal medium may be a bicarbonate buffer system.

The perfusion solution may comprise a buffered basal medium and at least one supplement selected from the group of: essential amino acids, non-essential amino acids, chemical energy substrates, nucleic acids, growth factors, hormones, lipids, colloids, oxygen carriers, vasodilators, purines and pyrimidines, attachment factors, antioxidants, impermeants and vitamins.

The perfusion solution may comprise: a buffered basal medium, essential amino acids, non-essential amino acids, chemical energy substrates, nucleic acids, growth factors, hormones, lipids, colloids, oxygen carriers, vasodilators, purines and pyrimidines, attachment factors, antioxidants, impermeants and vitamins.

In one embodiment, the perfusion solution comprises: buffered basal medium, essential amino acids, non-essential amino acids, nucleic acids, chemical energy substrates, growth factors, and vasodilators.

In one embodiment, the perfusion solution comprises: buffered basal medium, essential amino acids, non-essential amino acids, chemical energy substrates, growth factors, and vasodilators.

The perfusion solution may comprise at least one chemical energy substrate selected from: pyruvate, glucose, ATP, AMP, coenzyme A, flavin adenine dinucleotide (FAD), thiamine pyrophosphate chloride (cocarboxylase), β-nicotinamide adenine dinucleotide (NAD), β-nicotinamide adenine dinucleotide phosphate (NADP), uridine 5'triphosphate (UTP).

The perfusion solution may comprise at least one chemical energy substrate selected from: pyruvate, ATP, AMP, coenzyme A, flavin adenine dinucleotide (FAD), thiamine pyrophosphate chloride (cocarboxylase), β-nicotinamide adenine dinucleotide (NAD), β-nicotinamide adenine dinucleotide phosphate (NADP), uridine 5'triphosphate (UTP).

The perfusion solution may comprise at least one chemical energy substrate selected from: ATP, AMP, coenzyme A, flavin adenine dinucleotide (FAD), thiamine pyrophosphate chloride (cocarboxylase), β-nicotinamide adenine dinucleotide (NAD), β-nicotinamide adenine dinucleotide phosphate (NADP), uridine 5'triphosphate (UTP).

The perfusion solution may comprise at least one chemical energy substrate that includes at least one component of the citric acid cycle. In one embodiment, the perfusion solution may comprise at least one component selected from: coenzyme A, flavin adenine dinucleotide (FAD), β-nicotinamide adenine dinucleotide (NAD), β-nicotinamide adenine dinucleotide phosphate (NADP), and thiamine pyrophosphate chloride (cocarboxylase).

The perfusion solution may comprise at least one amino acid selected from: the basic set of 20 amino acids in the form of D- or L-amino acids (including alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine), and modified amino acids, such as citrulline, ornithine, homocysteine, homoserine, β-alanine, and amino-caproic acid.

The perfusion solution may comprise the amino acids alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine in the form of D- or L-amino acids.

The perfusion solution may comprise at least one nucleic acid for DNA repair and synthesis selected from: 2'deoxyadenosine, 2'deoxyguanosine, 2'deoxycytidine, adenosine, thymidine, guanosine, cytidine and uridine.

The perfusion solution may comprise at least one hormone selected from: insulin, and thyroid stimulating hormone (TSH). The perfusion solution may comprise the hormone insulin.

The perfusion solution may comprise at least one growth factor selected from: platelet-derived growth factor (PDGF), fibroblast growth factor (FGF-1, FGF-2), insulin-like growth factor I and II (IGF), epithelial growth factor, epidermal growth factor (EGF), brain-derived FGF, somatomedins A 1, A2, B and C, nerve growth factor (NGF), vascular endothelial growth factor (VEGF), heparin-binding growth factor (HBGF), endothelial cell growth factor (ECGF), and transforming growth factor (TGF), glucocorticoids, urogastone, IL-1, colony stimulating factor (CSF), erythropoietin, hepatoma growth factor and hepatocyte growth factor.

The perfusion solution may comprise at least one growth factor selected from: FGF-1 and FGF-2, and brain-derived FGF. The perfusion solution may comprise the growth factors FGF-1 and FGF-2, and brain-derived FGF.

The perfusion solution may comprise at least one growth factor selected from: FGF 1 & 2, VEGF, IGF and EGF.

The perfusion solution may comprise the growth factors FGF 1 & 2, VEGF, IGF and EGF.

The perfusion solution may comprise at least one growth factor selected from: FGF 1 & 2, VEGF, IGF, EGF, hepatoma growth factor and hepatocyte growth factor.

The perfusion solution may comprise the growth factors FGF 1 & 2, VEGF, IGF, EGF, hepatoma growth factor and hepatocyte growth factor.

The perfusion solution may comprise at least one lipid selected from: linoleic acid, arachidonic acid, linolenic acid, eicosapentaenoic acid, docosahexaenoic acid, oils, retinol acetate, cholesterol, calciferol and alpha tocopherol.

The perfusion solution may comprise at least one lipid selected from: retinol acetate, cholesterol, calciferol and alpha tocopherol.

The perfusion solution may comprise at least one colloid selected from: serum albumin, and mucopolysaccharides (such as chondroitin sulfate B, heparin, petastarch, hetastarch).

The perfusion solution may comprise at least one oxygen carrier that provides molecular oxygen for oxidative metabolism to the tissue or organ. The perfusion solution may comprise at least one oxygen carrier selected from: hemoglobin, stabilized hemoglobin derivatives (made from hemolyzed human erythrocytes such as pyridoxylated hemoglobin), polyoxethylene conjugates (PHP), recombinant hemoglobin products, and perfluorochemical (PFC) emulsions (such as perfluorooctyl bromide, perfluorooctyl dibromide, bromofluorocarbons, perfluoroethers, Fluosol DA™, F-44E, 1,2-bisperfluorobutyl-ethylene, F-4-methyl octahydroquinol-idizine, 9 to 12 carbon perfluoro amines, perfluorodecalin, perfluoroindane, perfluorotrimethyl bicycle[3,3,1]inane, perfluoromethyl adamante, perfluorodimethyl adamantine), and perfluorochemical microbubbles.

The perfusion solution may comprise hemoglobin or stabilized hemoglobin derivatives as the oxygen carrier. The perfusion solution may comprise a perfluorochemical (PFC) emulsion as the oxygen carrier. The perfusion solution may comprise a perfluorochemical (PFC) emulsion selected from at least one of: perfluorooctyl bromide, perfluorooctyldibromide, bromofluorocarbons, perfluoroethers, Fluosol DA™, F-44E, 1,2-bisperfluorobutyl-ethylene, F-4-methyl octahydroquinol-idizine, 9 to 12 carbon perfluoro amines, perfluorodecalin, perfluoroindane, perfluorotrimethyl bicycle[3,3,1]inane, perfluoromethyl adamante, perfluorodimethyl adamantine Red blood cells (RBC) may be used as an oxygen carrier in an effective amount to support metabolism by the organ being perfused (about 0.1% to 5% of the total perfusion solution). In one embodiment, the perfusion solution comprises about 1% of red blood cells.

The perfusion solution may comprise at least one vasodilator, which ensures that vasculature is well dilated, while simultaneously retaining its integrity and normal barrier function. The at least one vasodilator may be selected from: acetylcholine, dopamine, bradykinin, arginine (which promote endothelial cell mediated vasodilation); magnesium (eg. magnesium sulphate), prostacyclin, prostacyclin analogs (eg. carbacyclin) (which promote microvessel vasodilation), adenosine, adenosine analogs (eg. cyclohexyladenosine), verapamil, flunarizine, nifedipine, SNX-11, chlorpromazine, and diltiazem (which promote vascular dilation by mediating calcium channel blocking) and calcium ions (eg. calcium chloride).

The perfusion solution may comprise at least one vasodilator selected from: arginine, magnesium (eg. magnesium sulphate), adenosine and calcium ions (eg. calcium chloride).

The perfusion solution may comprise at least one impermeant selected from glutathione and cyclodextrin.

The perfusion solution may comprise at least one attachment factor, such as transferrin.

The perfusion solution may comprise at least one vitamin selected from: ascorbic acid, alpha tocopherol, biotin, calciferol, pantothenic acid, menadione, niacinamide, para-aminobenzoic acid, pyridoxal, pyridoxine, riboflavin and thiamine.

The perfusion solution may comprise at least one purine selected from: adenine (eg. adenine hemisulphate), guanine (eg. guanine HCl), xanthine (eg. xanthine Na) and hypoxanthine.

The perfusion solution may comprise at least one pyrimidine selected from: thymine, and uracil.

The supplements of the perfusion solution are used at a physiologically effective amount to support ex vivo oxidative metabolism by the organ or tissue.

The at least one chemical energy substrate may be pyruvate at a concentration of at least about 0.01 g/L. The at least one chemical energy substrate may be glucose at a concentration of at least about 0.1 g/L. The at least one chemical energy substrate may be ATP at a concentration of at least about 0.0001 g/L. The at least one chemical energy substrate may be AMP at a concentration of at least about 0.0001 g/L. The at least one chemical energy substrate may be coenzyme A at a concentration of at least about 0.001 g/L. The at least one chemical energy substrate may be flavin adenine dinucleotide (FAD) at a concentration of at least about 0.0001 g/L. The at least one chemical energy substrate may be thiamine pyrophosphate chloride (cocarboxylase) at a concentration of at least about 0.0001 g/L. The at least one chemical energy substrate may be β-nicotinamide adenine dinucleotide (NAD) at a concentration of at least about 0.001 g/L. The at least one chemical energy substrate may be β-nicotinamide adenine dinucleotide phosphate (NADP) at a concentration of at least about 0.0001 g/L. The at least one chemical energy substrate may be uridine 5'triphosphate (UTP) at a concentration of at least about 0.0001 g/L.

The at least one chemical energy substrate may be pyruvate used at a concentration of between about 0.01 g/L and 2 g/L. The at least one chemical energy substrate may be glucose used at a concentration of between about 0.1 g/L and 5 g/L. The at least one chemical energy substrate may be ATP used at a concentration of between about 0.0001 g/L and 0.02 g/L. The at least one chemical energy substrate may be AMP used at a concentration of between about 0.0001 g/L and 0.02 g/L. The at least one chemical energy substrate may be coenzyme A used at a concentration of between about 0.001 g/L and 0.1 g/L. The at least one chemical energy substrate may be flavin adenine dinucleotide (FAD) used at a concentration of between about 0.0001 g/L and 0.1 g/L. The at least one chemical energy substrate may be thiamine pyrophosphate chloride (cocarboxylase) used at a concentration of between about 0.0001 g/L and 0.1 g/L. The at least one chemical energy substrate may be β-nicotinamide adenine dinucleotide (NAD) used at a concentration of between about 0.001 g/L and 0.5 g/L. The at least one chemical energy substrate may be β-nicotinamide adenine dinucleotide phosphate (NADP) used at a concentration of between about 0.0001 g/L and 0.1 g/L. The at least one chemical energy substrate may be uridine 5'triphosphate (UTP) used at a concentration of between about 0.0001 g/L and 0.04 g/L.

The at least one amino acid may be used at a concentration of at least about 0.001 g/L. The at least one amino acid may be selected from alanine, arginine, asparagine, aspartic acid, cysteine, glutamine, glutamic acid, glycine, histidine, isoleucine, lysine, methionine, phenylalanine, proline, serine, threonine, tryptophan, tyrosine and valine with a concentration of at least about 0.001 g/L. The at least one amino acid may be Leucine with a concentration of at least about 0.01 g/L.

The at least one amino acid may be used at a concentration of between about 0.001 g/L and 5 g/L. The at least one amino acid may be selected from alanine, arginine, asparagine, aspartic acid, cysteine, glutamine, glutamic acid, glycine, histidine, isoleucine, lysine, methionine, phenylalanine, proline, serine, threonine, tryptophan, tyrosine and valine with a concentration of between about 0.001 g/L and 5 g/L. The at least one amino acid may be Leucine used at a concentration of between about 0.01 g/L and 5 g/L.

The at least one nucleic acid may be used at a concentration of at least about 0.001 g/L. The at least one nucleic acid may be selected from 2'deoxyadenosine, 2'deoxyguanosine, 2'deoxycytidine, adenosine, thymidine, guanosine, cytidine and uridine at a concentration of at least about 0.001 g/L.

The at least one nucleic acid may be used at a concentration of between about 0.001 g/L and 0.4 g/L. The at least one nucleic acid may be selected from 2'deoxyadenosine, 2'deoxyguanosine, 2'deoxycytidine, adenosine, thymidine, guanosine, cytidine and uridine at a concentration of between about 0.001 g/L and 0.4 g/L.

The at least one hormone may be used at a concentration of at least about 0.001 g/L. The at least one hormone may be insulin at a concentration of at least about 0.001 g/L.

The at least one hormone may be used at a concentration of between about 0.001 g/L and 0.4 g/L. The at least one hormone may be insulin at a concentration of between about 0.001 g/L and 0.4 g/L.

The at least one growth factor may be used at a concentration of at least about 0.002 g/L. The at least one growth factor may be used at a concentration of between about 0.002 g/L and 0.4 g/L. The perfusion solution may comprise the growth factors FGF 1 & 2, VEGF, IGF and EGF at a combined concentration of at least about 0.002 g/L. The perfusion solution may comprise the growth factors FGF 1 & 2, VEGF, IGF and EGF at a combined concentration of between about 0.002 g/L and 0.4 g/L.

The at least one lipid may be retinol acetate used at a concentration of at least about 0.00001 g/L. The at least one lipid may cholesterol used at a concentration of at least about 0.00001 g/L. The at least one lipid may calciferol used at a concentration of at least about 0.00001 g/L. The at least one lipid may alpha tocopherol used at a concentration of at least about 0.000001 g/L.

The at least one lipid may retinol acetate used at a concentration of between about 0.00001 g/L and about 1 g/L. The at least one lipid may cholesterol used at a concentration of between about 0.00001 g/L and 1 g/L. The at least one lipid may calciferol used at a concentration of between about 0.00001 g/L and 1 g/L. The at least one lipid may alpha tocopherol used at a concentration of between about 0.000001 g/L and 1 g/L.

The at least one colloid may be serum albumin used at a concentration of at least about 5 g/L. The at least one colloid may be mucopolysaccharide used at a concentration of at least about 0.001 g/L.

The at least one colloid may be serum albumin used at a concentration of between about 5 g/L and 40 g/L. The at least one colloid may be mucopolysaccharide used at a concentration of between about 0.001 g/L and 0.9 g/L.

The at least one oxygen carrier may comprise between 0% and 20% of the total perfusion solution (v/v). The at least one oxygen carrier may be chemically modified hemoglobin and may comprise between 0% and 20% of the total perfusion solution (v/v). The at least one oxygen carrier may be chemically modified hemoglobin used at a concentration of between about 0 g/L and 216 g/L. The at least one oxygen carrier may be chemically modified hemoglobin used at a concentration of at least about 200 g/L. The at least one oxygen carrier may be chemically modified hemoglobin used at a concentration of about 200 g/L.

The at least one oxygen carrier may be perfluorochemical emulsion and may comprise between 0% and 20% of the total perfusion solution (v/v). The at least one oxygen carrier may be perfluorochemical emulsion may comprise between 0% and 20% of the total perfusion solution (v/v). The at least one oxygen carrier may be perfluorochemical emulsion used at a concentration of between about 0 g/L and 216 g/L. The at least one oxygen carrier may be perfluorochemical emulsion used at a concentration of at least about 200 g/L. The at least one oxygen carrier may be perfluorochemical emulsion used at a concentration of about 200 g/L.

The at least one oxygen carrier may red blood cells (RBC) used at a concentration of between about 0.1% to 5% of the total perfusion solution (v/v).

The at least one vasodilator may be arginine used at a concentration of at least about 0.001 g/L. The at least one vasodilator may be magnesium (eg. magnesium sulphate) used at a concentration of at least about 0.001 g/L. The at least one vasodilator may be adenosine used at a concentration of at least about 0.001 g/L. The at least one vasodilator may be calcium ions (eg. calcium chloride) used at a concentration of at least about 0.01 g/L.

The at least one vasodilator may be arginine used at a concentration of between about 0.001 g/L and about 5 g/L. The at least one vasodilator may be magnesium (eg. magnesium sulphate) used at a concentration of between about 0.001 g/L and 5 g/L. The at least one vasodilator may be adenosine used at a concentration of between about 0.001 g/L and 0.4 g/L. The at least one vasodilator may be calcium ions (eg. calcium chloride) used at a concentration of between about 0.01 g/L and 2.5 g/L.

The at least one impermeant may be glutathione used at a concentration of at least about 0.000001 g/L. The at least one impermeant may be cyclodextrin used at a concentration of at least about 0.01 g/L.

The at least one impermeant may be glutathione used at a concentration between about 0.000001 g/L and 1 g/L. The at least one impermeant may be cyclodextrin used at a concentration between about 0.01 g/L and 5 g/L.

The at least one attachment factor may be transferrin used at a concentration of at least about 0.001 g/L. The at least one attachment factor may be transferrin used at a concentration of between about 0.001 g/L and 0.8 g/L.

The at least one vitamin may be ascorbic acid used at a concentration of at least about 0.000001 g/L. The at least one vitamin may be alpha tocopherol used at a concentration of at least about 0.000001 g/L. The at least one vitamin may be biotin used at a concentration of at least about 0.000001 g/L. The at least one vitamin may be calciferol used at a concentration of at least about 0.00001 g/L. The at least one vitamin may be pantothenic acid used at a concentration of at least about 0.000001 g/L. The at least one vitamin may be menadione used at a concentration of at least about 0.000001 g/L. The at least one vitamin may be niacinamide used at a concentration of at least about 0.000001 g/L. The at least one vitamin may be para-aminobenzoic acid used at a concentration of at least about 0.000001 g/L. The at least one vitamin may be pyridoxal used at a concentration of at least about 0.000001 g/L. The at least one vitamin may be pyridoxine used at a concentration of at least about 0.000001 g/L. The at least one vitamin may be riboflavin used at a concentration of at least about 0.000001 g/L. The at least one vitamin may be thiamine used at a concentration of at least about 0.000001 g/L.

The at least one vitamin may be ascorbic acid used at a concentration of between about 0.000001 g/L and 1 g/L. The at least one vitamin may be alpha tocopherol used at a concentration of between about 0.000001 g/L and 1 g/L. The at least one vitamin may be biotin used at a concentration of between about 0.000001 g/L and 1 g/L. The at least one vitamin may be calciferol used at a concentration of between about 0.00001 g/L and 1 g/L. The at least one vitamin may be pantothenic acid used at a concentration of between about 0.000001 g/L and 1 g/L. The at least one vitamin may be menadione used at a concentration of between about 0.000001 g/L and 1 g/L. The at least one vitamin may be niacinamide used at a concentration of between about 0.000001 g/L and 1 g/L. The at least one vitamin may be para-aminobenzoic acid used at a concentration of between about 0.000001 g/L and 1 g/L. The at least one vitamin may be pyridoxal used at a concentration of between about 0.000001 g/L and 1 g/L. The at least one vitamin may be pyridoxine used at a concentration of between about 0.000001 g/L and 1 g/L. The at least one vitamin may be riboflavin used at a concentration of between about 0.000001 g/L and 1 g/L. The at least one vitamin may be thiamine used at a concentration of between about 0.000001 g/L and 1 g/L.

The at least one purine may be adenine (eg. adenine hemisulphate) used at a concentration of at least about 0.001 g/L. The at least one purine may be guanine (eg. guanine HCl) used at a concentration of at least about 0.00001 g/L. The at least one purine may be xanthine (eg. xanthine Na) used at a concentration of at least about 0.00001 g/L. The at least one purine may be hypoxanthine used at a concentration of at least about 0.00001 g/L.

The at least one purine may be adenine (eg. adenine hemisulphate) used at a concentration of between about 0.001 g/L and 5 g/L. The at least one purine may be guanine (such as guanine HCl) used at a concentration of between about 0.00001 g/L and 1 g/L. The at least one purine may be xanthine (eg. xanthine Na) used at a concentration of between about 0.00001 g/L and 1 g/L. The at least one purine may be hypoxanthine used at a concentration of between about 0.00001 g/L and 1 g/L.

The at least one pyrimidine may be thymine used at a concentration of at least about 0.00001 g/L. The at least one pyrimidine may be uracil used at a concentration of at least about 0.00001 g/L.

The at least one pyrimidine may be thymine used at a concentration of between about 0.00001 g/L and 1 g/L. The at least one pyrimidine may be uracil used at a concentration of between about 0.00001 g/L and 1 g/L.

The perfusion solution supports the nutritional needs and metabolic needs of the vascular endothelium within the tissue or organ, thereby maintaining the vasculature and the normal permeability of the tissue or organ.

The perfusion solution maintains the cellular environment at physiologic and maintains near normal oxygenation, temperature, and osmolarity.

The perfusion solution maintains the normal barrier function of the tissue to macromolecules, thereby resulting in stable perfusion pressures and stable vasculature flow rates.

The perfusion solution adequately dilates and fills the vasculature, delivers adequate trophic factors to maintain a near normal level of metabolism in the isolated organ or section of anatomy and supports the artificially interrupted aerobic metabolism by providing high energy compounds.

The perfusion solution potentiates the simultaneous growth of microvessel and large vessel endothelial cells, to support the integrity of vascular endothelium within a graft; and to support normal permeability and metabolism without extreme hypothermia.

In one embodiment, the enhanced ability of the solution to serve as a preservation solution for organs for transplantation using a warm preservation technology, may be attributed to supplementation with serum albumin as a source of protein and colloid, vasodilators to ensure adequate dilation of the vasculature, trace elements to potentiate viability and cellular function, pyruvate and adenosine for oxidative phosphorylation support; transferrin as an attachment factor; insulin and sugars for metabolic support; and glutathione to scavenge toxic free radicals as well as a source of impermeant; cyclodextrin as a source of impermeant, scavenger and potentiator of cell attachment and growth factors; a high Mg concentration for microvessel metabolism support; mucopolysaccharides, comprising primarily chondroitin sulfates and heparin sulfates, for growth factor potentiation and hemostasis; and ENDO GRO™ as a source of colloid, impermeant and growth promoter. ENDO GRO™ is a formulation that contains a combination of at least the following growth factors: FGF 1 & 2, VEGF, IGF and EGF.

The perfusion solution provides the necessary components required to support oxidative metabolism of the tissue or organ. The perfusion solution supports ongoing oxidative metabolism with supplemental substrates that may include, but are not limited to, glucose, pyruvate, and uridine 5-triphosphate (UTP). The ongoing oxidative metabolism may be further supported by maintaining the adenine compound pool. The citric acid cycle and the electron transport chain are supported by providing adequate substrate delivery to continue metabolic support and function in the isolated organ and tissues. The ongoing metabolism supported by the perfusion solution and system provides adequate metabolites and nutrients to maintain the tissue integrity with tight cellular functions and normal membrane polarity.

Supplements relating to ATP synthesis can be useful for promoting the generation of energy resources needed to facilitate passenger leukocyte migration.

In one embodiment, the perfusion solution comprises a buffered basal medium, and at least one supplement selected from: glucose, ribose, deoxyribose, glutamine, glycine, aspartate, adenosine, adenine, adenosine 5'triphosphate and adenosine 5'monophosphate.

In one embodiment, the perfusion solution comprises a buffered basal medium, glucose, ribose, deoxyribose, glutamine, glycine, aspartate, adenosine, adenine, adenosine 5'triphosphate and adenosine 5'monophosphate.

This particular combination of supplements advantageously promotes ATP synthesis. This is important for ensuring that the leukocytes present within the donor tissue or organ have sufficient energy resources to migrate out of the tissue or organ into the perfusion solution that is circulating within the perfusion system. Example 6 demonstrates that the provision of these additional nutrients in the perfusion solution enables a significant increase in the production of ATP by the tissue or organ, thereby facilitating migration of the donor passenger leukocytes for collection (see FIG. 5).

In one embodiment, the perfusion solution comprises: a buffered basal medium; essential amino acids, non-essential amino acids, chemical energy substrates, nucleic acids, growth factors, hormones, lipids, colloids, oxygen carriers, vasodilators, purines and pyrimidines, attachment factors, antioxidants, impermeants and vitamins; and the following specific supplements: glucose, ribose, deoxyribose, glutamine, glycine, aspartate, adenosine, adenine, adenosine 5'triphosphate and adenosine 5'monophosphate.

In one embodiment, the perfusion solution comprises: a buffered basal medium; essential amino acids, non-essential amino acids, chemical energy substrates, nucleic acids, growth factors, hormones, lipids, colloids, oxygen carriers, vasodilators, purines and pyrimidines, attachment factors, antioxidants, impermeants and vitamins; and the following specific supplements: glucose, ribose, deoxyribose, glutamine, glycine, aspartate, adenosine, adenine, adenosine 5'triphosphate, adenosine 5'monophosphate, pyruvate, ATP, AMP, coenzyme A, flavin adenine dinucleotide (FAD), thiamine pyrophosphate chloride (cocarboxylase), β-nicotinamide adenine dinucleotide (NAD), β-nicotinamide adenine dinucleotide phosphate (NADP), uridine 5'triphosphate (UTP).

In one embodiment, the perfusion solution comprises a buffered basal medium, essential amino acids, non-essential amino acids, nucleic acids, chemical energy substrates, growth factors, and vasodilators; and the following specific supplements: glucose, ribose, deoxyribose, glutamine, glycine, aspartate, adenosine, adenine, adenosine 5'triphosphate and adenosine 5'monophosphate.

In one embodiment, the perfusion solution comprises a buffered basal medium, essential amino acids, non-essential amino acids, nucleic acids, chemical energy substrates, growth factors, and vasodilators; and the following specific supplements: glucose, ribose, deoxyribose, glutamine, glycine, aspartate, adenosine, adenine, adenosine 5'triphosphate, adenosine 5'monophosphate, pyruvate, ATP, AMP, coenzyme A, flavin adenine dinucleotide (FAD), thiamine pyrophosphate chloride (cocarboxylase), β-nicotinamide adenine dinucleotide (NAD), β-nicotinamide adenine dinucleotide phosphate (NADP), uridine 5'triphosphate (UTP).

In one embodiment, the perfusion solution comprises a buffered basal medium, essential amino acids, non-essential amino acids, chemical energy substrates, growth factors, and vasodilators; and the following specific supplements: glucose, ribose, deoxyribose, glutamine, glycine, aspartate, adenosine, adenine, adenosine 5'triphosphate and adenosine 5'monophosphate.

In one embodiment, the perfusion solution comprises a buffered basal medium, essential amino acids, non-essential amino acids, chemical energy substrates, growth factors, and vasodilators; and the following specific supplements: glucose, ribose, deoxyribose, glutamine, glycine, aspartate, adenosine, adenine, adenosine 5'triphosphate, adenosine 5'monophosphate, pyruvate, ATP, AMP, coenzyme A, flavin adenine dinucleotide (FAD), thiamine pyrophosphate chloride (cocarboxylase), β-nicotinamide adenine dinucleotide (NAD), β-nicotinamide adenine dinucleotide phosphate (NADP), uridine 5'triphosphate (UTP).

The ATP synthesis supplements may be used in the perfusion solution at the following concentrations:
(a) glucose at a concentration of between 1-3 g/L;
(b) ribose at a concentration of between 5-15 mg/L;
(c) deoxyribose at a concentration of between 5-15 mg/L;
(d) glutamine at a concentration of between 150-250 mg/L;
(e) glycine at a concentration of between 50-150 mg/L;
(f) aspartate at a concentration of between 80-160 mg/L;
(g) adenosine at a concentration of 2-6 mg/L;
(h) adenine at a concentration of 10-30 mg/L;
(i) adenosine 5'triphosphate at a concentration of 35-45 mg/L; and
(j) adenosine 5'monophosphate at a concentration of 2-6 mg/L.

In one embodiment, the ATP synthesis supplements are used in the perfusion solution at the following concentrations:
(a) glucose at a concentration of 2 g/L;
(b) ribose at a concentration of 10 mg/L;
(c) deoxyribose at a concentration of 10 mg/L;
(d) glutamine at a concentration of 200 mg/L;
(e) glycine at a concentration of 100 mg/L;
(f) aspartate at a concentration of 120 mg/L;
(g) adenosine at a concentration of 4 mg/L;
(h) adenine at a concentration of 20 mg/L;
(i) adenosine 5'triphosphate at a concentration of 38 mg/L;
(j) adenosine 5'monophosphate at a concentration of 4 mg/L.

In all embodiments of the perfusion solution described above, the buffered basal medium; essential amino acids, non-essential amino acids, chemical energy substrates, nucleic acids, growth factors, hormones, lipids, colloids, oxygen carriers, vasodilators, purines and pyrimidines, attachment factors, antioxidants, impermeants and vitamins may be selected from those defined above, and may be present in the perfusion solution at the concentrations defined above.

In one embodiment, the perfusion solution comprises a composition as defined in Table 1. Each of the components may be present at a concentration as defined in the Table.

Table 1:

| Component | Basal media ranges |
| --- | --- |
| DL-Alanine | 0.001-5 g/L |
| L-Arginine HC 1 | 0.001-5 g/L |
| DL-Aspartic Acid | 0.001-5 g/L |
| L-Cysteine HCL•H$_2$0 | 0.0001-1 g/L |
| L-Cystine 2HC 1 | 0.001-5 g/L |
| DL-Glutamic Acid | 0.001-5 g/L |
| L-Glutamine | 0.001-5 g/L |
| Glycine | 0.001-5 g/L |
| L-Histidine HCl•H$_2$0 | 0.001-5 g/L |
| L-Hydroxyproline | 0.001-5 g/L |
| DL-Isoleucine | 0.001-5 g/L |
| DL-Leucine | 0.01-5 g/L |
| L-Lysine HCl | 0.001-5 g/L |
| DL-Methionine | 0.001-5 g/L |
| DL-Phenylalanine | 0.001-5 g/L |
| L-Proline | 0.001-5 g/L |
| DL-Serine | 0.001-5 g/L |
| DL-Threonine | 0.001-5 g/L |
| DL-Tryptophan | 0.001-5 g/L |
| L-Tyrosine•2Na | 0.001-5 g/L |
| DL-Valine | 0.001-5 g/L |
| Adenine Hemisulfate | 0.001-5 g/L |
| Adenosine Triphosphate•2Na | 0.0001-1 g/L |
| Adenylic Acid | 0.00001-1 g/L |
| Alpha Tocopherol Phosphate•2Na | 0.000001-1 g/L |
| Ascorbic Acid | 0.000001-1 g/L |
| D-Biotin | 0.000001-1 g/L |
| Calciferol | 0.00001-1 g/L |
| Cholesterol | 0.00001-1 g/L |
| Choline Chloride | 0.00001-1 g/L |
| Deoxyribose | 0.00001-1 g/L |
| Folic Acid | 0.000001-1 g/L |
| Glutathione (Reduced) | 0.000001-1 g/L |
| Guanine HCl | 0.00001-1 g/L |
| Hypoxanthine | 0.00001-1 g/L |
| Menadione (Na bisulfite) | 0.000001-1 g/L |
| Myo-Inositol | 0.000001-1 g/L |
| Niacinamide | 0.000001-1 g/L |
| Nicotinic Acid | 0.000001-1 g/L |
| PABA | 0.000001-1 g/L |
| D-Pantothenic Acid Ca | 0.000001-1 g/L |
| Polyoxyethylenesorbitan Monoleate | 0.001-1 g/L |
| Pyridoxal HC 1 | 0.000001-1 g/L |
| Pyridoxine HC 1 | 0.000001-1 g/L |
| Retinol Acetate | 0.00001-1 g/L |
| Riboflavin | 0.000001-1 g/L |
| Ribose | 0.00001-1 g/L |
| Thiamine HC 1 | 0.000001-1 g/L |
| Thymine | 0.00001-1 g/L |
| Uracil | 0.00001-1 g/L |
| Xanthine Na | 0.00001-1 g/L |
| Calcium Chloride•2H$_2$0 | 0.01-2.5 g/L |
| Ferric Nitrate•9H$_2$0 | 0.00001-1 g/L |
| Magnesium sulfate (anhydrous) | 0.001-5 g/L |
| Potassium chloride | 0.01-5 g/L |
| Sodium Acetate (anhydrous) | 0.001-5 g/L |
| Sodium Chloride | 1-10 g/L |
| Sodium Phosphate Monobasic(anhydrous) | 0.01-5 g/L |
| Glucose | 0.1-5 g/L |
| Insulin | 0.001-0.4 g/L |
| Serum albumin | 5-40 g/L |
| NaHC03 | 0.5-4.4 g/L |
| Pyruvate | 0.01-2.0 g/L |
| Transferrin | 0.001-0.8 g/L |
| Serum | 1-100 ml/L |
| Impermeant (cycledextrin) | 0.01-5.0 g/L |
| Mucopolysaccharide (chondroitin sulfate B) | 0.001-0.9 g/L |
| ENDO GRO ™ (growth factor) | 0.002-0.4 g/L |
| heparin | 0.01-0.8 g/L |
| chemically modified hemaglobin* orperfluorochemical emulsion* | 0-216 mg/L |
| Coenzyme A | 0.001-0.1 g/L |
| FAD | 0.0001-0.1 g/L |
| NAD | 0.001-0.5 g/L |
| Cocarboxylase | 0.0001-0.1 g/L |
| NADP | 0.0001-0.1 g/L |
| 2'deoxyadenosine | 0.001-0.4 g/L |
| 2'deoxyguanosine | 0.001-0.4 g/L |
| 2'deoxycytidine | 0.001-0.4 g/L |
| thymidine | 0.001-0.4 g/L |
| adenosine | 0.001-0.4 g/L |
| guanosine | 0.001-0.4 g/L |
| cytidine | 0.001-0.4 g/L |
| uridine | 0.001-0.4 g/L |
| ATP | 0.0001-0.02 g/L |
| AMP | 0.0001-0.02 g/L |
| UTP | 0.0001-0.04 g/L |

*As an oxygen carrier

In one embodiment, the perfusion solution comprises the composition according to that defined in Table 1, with the exception that the supplements referred to below are present in the amount specified below:
(a) glucose at a concentration of between 1-3 g/L;
(b) ribose at a concentration of between 5-15 mg/L;
(c) deoxyribose at a concentration of between 5-15 mg/L;
(d) glutamine at a concentration of between 150-250 mg/L;
(e) glycine at a concentration of between 50-150 mg/L;
(f) aspartate at a concentration of between 80-160 mg/L;
(g) adenosine at a concentration of 2-6 mg/L;

(h) adenine at a concentration of 10-30 mg/L;
(i) adenosine 5'triphosphate at a concentration of 35-45 mg/L; and
(j) adenosine 5'monophosphate at a concentration of 2-6 mg/L.

In one embodiment, the perfusion solution comprises a composition as defined in Table 2. Each of the components may be present at a concentration as defined in the Table. Table 2:

| Component | Formulation |
| --- | --- |
| DL-Alanine | 0.12 g/L |
| L-Arginine HC 1 | 0.14 g/L |
| DL-Aspartic Acid | 0.12 g/L |
| L-Cysteine HCL•H$_2$0 | 0.022 g/L |
| L-Cystine 2HC 1 | 0.052 g/L |
| DL-Glutamic Acid | 0.2672 g/L |
| L-Glutamine | 0.2 g/L |
| Glycine | 0.1 g/L |
| L-Histidine HCl•H$_2$O | 0.04376 g/L |
| L-Hydroxyproline | 0.02 g/L |
| DL-Isoleucine | 0.08 g/L |
| DL-Leucine | 0.24 g/L |
| L-Lysine HCl | 0.14 g/L |
| DL-Methionine | 0.06 g/L |
| DL-Phenylalanine | 0.10 g/L |
| L-Proline | 0.08 g/L |
| DL-Serine | 0.10 g/L |
| DL-Threonine | 0.12 g/L |
| DL-Tryptophan | 0.04 g/L |
| L-Tyrosine•2Na | 0.11532 g/L |
| DL-Valine | 0.10 g/L |
| Adenine Hemisulfate | 0.02 g/L |
| Adenosine Triphosphate•2Na | 0.002 g/L |
| Adenylic Acid | 0.0004 g/L |
| Alpha Tocopherol Phosphate•2Na | 0.00002 g/L |
| Ascorbic Acid | 0.0001 g/L |
| D-Biotin | 0.00002 g/L |
| Calciferol | 0.0002 g/L |
| Cholesterol | 0.0024 g/L |
| Choline Chloride | 0.001 g/L |
| Deoxyribose | 0.001 g/L |
| Folic Acid | 0.00002 g/L |
| Glutathione (Reduced) | 0.0001 g/L |
| Guanine HCl | 0.0006 g/L |
| Hypoxanthine | 0.0006 g/L |
| Menadione (Na bisulfite) | 0.00003 g/L |
| Myo-Inositol | 0.00011 g/L |
| Niacinamide | 0.00005 g/L |
| Nicotinic Acid | 0.00005 g/L |
| PABA | 0.0001 g/L |
| D-Pantothenic Acid Ca | 0.00002 g/L |
| Polyoxyethylenesorbitan Monoleate | 0.04 g/L |
| Pyridoxal HC 1 | 0.00005 g/L |
| Pyridoxine HC 1 | 0.00005 g/L |
| Retinol Acetate | 0.00028 g/L |
| Riboflavin | 0.00002 g/L |
| Ribose | 0.001 g/L |
| Thiamine HC 1 | 0.00002 g/L |
| Thymine | 0.0006 g/L |
| Uracil | 0.0006 g/L |
| Xanthine Na | 0.00069 g/L |
| Calcium Chloride•2H$_2$0 | 0.265 g/L |
| Ferric Nitrate•9H$_2$0 | 0.00144 g/L |
| Magnesium sulfate (anhydrous) | 1.20 g/L |
| Potassium chloride | 0.4 g/L |
| Sodium Acetate (anhydrous) | 0.1 g/L |
| Sodium Chloride | 6.8 g/L |
| Sodium Phosphate Monobasic(anhydrous) | 0.244 g/L |
| Glucose | 2.0 g/L |
| Insulin | 0.01 g/L |
| Serum albumin | 30.0 g/L |
| NaHC03 | 4.4 g/L |
| Pyruvate | 0.22 g/L |
| Transferrin | 0.1 g/L |
| Serum | 100 ml |
| Impermeant (cyclodextrin) | 0.5 g/L |
| Mucopolysaccharide (chondroitin sulfate B) | 0.004 g/L |
| ENDO GRO ™ (growth factor) | 0.020 g/L |
| heparin | 0.18 g/L |
| chemically modified hemaglobin* or | 216 mg/L 20% (v/v) |
| Coenzyme A | 0.010 g/L |
| FAD | 0.004 g/L |
| NAD | 0.028 g/L |
| Cocarboxylase | 0.004 g/L |
| NADP | 0.004 g/L |
| 2'deoxyadenosine | 0.042 g/L |
| 2'deoxyguanosine | 0.042 g/L |
| 2'deoxycytidine | 0.042 g/L |
| thymidine | 0.042 g/L |
| adenosine | 0.042 g/L |
| guanosine | 0.042 g/L |
| cytidine | 0.042 g/L |
| uridine | 0.042 g/L |
| ATP | 0.002 g/L |
| AMP | 0.002 g/L |
| UTP | 0.004 g/L |

*As an oxygen carrier

In one embodiment, the perfusion solution comprises the composition according to that defined in Table 2, with the exception that the supplements referred to below are present in the amount specified below:

(a) glucose at a concentration of 2 g/L;
(b) ribose at a concentration of 10 mg/L;
(c) deoxyribose at a concentration of 10 mg/L;
(d) glutamine at a concentration of 200 mg/L;
(e) glycine at a concentration of 100 mg/L;
(f) aspartate at a concentration of 120 mg/L;
(g) adenosine at a concentration of 4 mg/L;
(h) adenine at a concentration of 20 mg/L;
(i) adenosine 5'triphosphate at a concentration of 38 mg/L;
(j) adenosine 5'monophosphate at a concentration of 4 mg/L.

As used herein, the phrase "migrate from the tissue or organ into the recirculating perfusion solution" refers to the energy dependent process by which donor passenger leukocytes exit the tissue or organ into the recirculating perfusion solution.

In one embodiment, substantially all the donor passenger leukocytes within the tissue or organ migrate into the recirculating perfusion solution. In one embodiment, at least 20% of the donor passenger leukocytes present within the donor tissue or organ migrate from the tissue or organ into the recirculating perfusion solution. In one embodiment, at least 30% of the donor passenger leukocytes present within the donor tissue or organ migrate from the tissue or organ into the recirculating perfusion solution. In one embodiment, at least 40% of the donor passenger leukocytes present within the donor tissue or organ migrate from the tissue or organ into the recirculating perfusion solution. In one embodiment, at least 50% of the donor passenger leukocytes present within the donor tissue or organ migrate from the tissue or organ into the recirculating perfusion solution. In one embodiment, at least 60% of the donor passenger leukocytes present within the donor tissue or organ migrate from the tissue or organ into the recirculating perfusion solution. In one embodiment, at least 70% of the donor passenger leukocytes present within the donor tissue or organ migrate from the tissue or organ into the recirculating perfusion solution. In one embodiment, at least 80% of the donor passenger leukocytes present within the donor tissue or organ migrate from the tissue or organ into the recirculating perfusion solution. In one embodiment, at least 90% of the donor passenger leukocytes present within the donor tissue or organ migrate from the tissue or organ into the recirculating perfusion solution. In one embodiment, at least 95% of the donor passenger leukocytes present within the donor tissue or organ migrate from the tissue or organ into the recirculating perfusion solution. In one embodiment, at least 98% of the donor passenger leukocytes present within the donor tissue or organ migrate from the tissue or organ into the recirculating perfusion solution.

As used herein, the phrase "isolating the passenger leukocytes from the recirculating perfusion solution" refers to the process by which donor passenger leukocytes are isolated and removed from the recirculating perfusion solution.

In one embodiment, substantially all the donor passenger leukocytes present within the recirculating perfusion solution are isolated and removed from the recirculating perfusion solution. In one embodiment, at least 20% of the donor passenger leukocytes present within the recirculating perfusion solution are isolated and removed from the recirculating perfusion solution. In one embodiment, at least 30% of the donor passenger leukocytes present within the recirculating perfusion solution are isolated and removed from the recirculating perfusion solution. In one embodiment, at least 40% of the donor passenger leukocytes present within the recirculating perfusion solution are isolated and removed from the recirculating perfusion solution. In one embodiment, at least 50% of the donor passenger leukocytes present within the recirculating perfusion solution are isolated and removed from the recirculating perfusion solution. In one embodiment, at least 60% of the donor passenger leukocytes present within the recirculating perfusion solution are isolated and removed from the recirculating perfusion solution. In one embodiment, at least 70% of the donor passenger leukocytes present within the recirculating perfusion solution are isolated and removed from the recirculating perfusion solution. In one embodiment, at least 80% of the donor passenger leukocytes present within the recirculating perfusion solution are isolated and removed from the recirculating perfusion solution. In one embodiment, at least 90% of the donor passenger leukocytes present within the recirculating perfusion solution are isolated and removed from the recirculating perfusion solution. In one embodiment, at least 95% of the donor passenger leukocytes present within the recirculating perfusion solution are isolated and removed from the recirculating perfusion solution. In one embodiment, at least 98% of the donor passenger leukocytes present within the recirculating perfusion solution are isolated and removed from the recirculating perfusion solution. In one embodiment, 100% of the donor passenger leukocytes present within the recirculating perfusion solution are isolated and removed from the recirculating perfusion solution.

In one embodiment, the passenger leukocytes may be removed from the recirculating perfusion solution using filtration. Filtration provides a simple approach to remove cells from the recirculating perfusion solution. Filtration may be performed using a porous membrane. The pore size of the membrane is sufficient to isolate passenger leukocytes (which are between 10 µm to 17 µm) from the recirculating perfusion solution. In one embodiment the pore size of the membrane is between about 1 µm to about 10 µm. Alternatively, the pore size of the membrane may be between about 2 µm to about 10 µm, such as between about 3 µm to about 10 µm, between about 4 µm to about 10 µm, or between about 5 µm to about 10 µm. In one embodiment, the pore size of the membrane is about 5 µm.

The membrane of the filter may be located within an in-line cell processor in the perfusion system. The transmembrane pressure of the filter is maintained by the perfusion system's circulating mean pressures and its associated vascular flow rates. The isolated donor passenger leukocytes may be isolated from a chamber located above the filter membrane by aspiration with a syringe.

In one embodiment, the passenger leukocytes may be removed from the recirculating perfusion solution by centrifugation. A flow device may be used to isolate the passenger leukocytes by subjecting the recirculating perfusion solution to a centrifugal force that results in a cell gradient allowing the passenger leukocytes to be removed from the perfusate.

In one embodiment, the passenger leukocytes may be removed from the recirculating perfusion solution using apheresis techniques.

In one embodiment, the passenger leukocytes may be removed from the recirculating perfusion solution using magnetic beads. In one embodiment, magnetic beads conjugated to antibodies that are specific for markers on the passenger leukocyte cell surface may be used to separate the passenger leukocytes from the recirculating perfusion solution.

Once the passenger leukocytes have been isolated from the recirculating perfusion solution, they can be concentrated by centrifugation.

As used herein, the term "reducing the immunogenicity of a tissue or organ" means reducing the ability of the donor tissue or organ to promote an immune response in the recipient patient.

As used herein, the term "reducing the immunogenicity of donor passenger leukocytes" means reducing the ability of the donor passenger leukocytes to activate T lymphocytes in the recipient patient.

As used herein, the term "immune rejection" refers to the process by which the immune system of a recipient patient responds to a transplanted tissue or organ, leading to destruction of the tissue or organ.

As used herein, the term "treating" refers to the process of applying an agent that blocks the ability of passenger leukocytes to co-stimulate T cell activation. In one embodiment, the treatment step is performed on passenger leukocytes that have been isolated from the donor tissue or organ. In one embodiment, the treatment step is performed whilst a donor tissue or organ is in a warm perfusion system, and passenger leukocytes are located either in situ in the tissue or organ or are circulating in the perfusion solution.

The ability of passenger leukocytes to co-stimulate activation of T cells can be investigated by a standard bromodeoxyuridine proliferation assay, as illustrated in Example 4. Other assays for testing the co-stimulatory activity of the passenger leukocytes are available in the art; including the tritiated thymidine assay, as described in Davies, J. K. et al.; Induction of Alloantigen-specific Anergy in Human Peripheral Blood Mononuclear Cells by Alloantigen Stimulation with Co-stimulatory Signal Blockade; *J. Vis. Exp.;* 49; e2673; (2011); Barbon, C. M. et al.; Alloanergization of Human T Cells Results in Expansion of Alloantigen-Specific CD8$^+$CD28$^-$ Suppressor Cells; *American Journal of Transplantation;* 14; p 305-318; (2014); and Coenen J J et al.; CTLA-4 engagement and regulatory CD4CD25T cells independently control CD8-mediated responses undercostimulation blockade; *J Immunol;* 176; p 5240-5246; (2006). Flow cytometry can also be used to determine the co-stimulatory activity of the passenger leukocytes, as described in Verghese, D. A. et al.; Costimulatory Blockade-Induced Allograft Survival Requires Beclin1; *American Journal of Transplantation;* 14; p 545-553; (2014).

The treatment process may include incubating the isolated passenger leukocytes with the agent for at least 5 minutes, at least 10 minutes, at least 20 minutes, at least 40 minutes, at least 1 hour, at least 6 hours, at least 12 hours, or at least 24 hours. In one embodiment, the treatment process is performed for at least 5 minutes.

The treatment process may include incubating the isolated passenger leukocytes with the agent for up to 30 minutes, 1 hour, 6 hours, 12 hours, 24 hours, 36 hours or 48 hours. In one embodiment, the treatment is performed for up to 30 minutes.

As used herein, the term "agent" means any biological molecule or chemical compound that has the ability to block the co-stimulatory activity of passenger leukocytes.

The treatment process may involve treating the passenger leukocytes with an agent that reduces or inhibits the expression or activity of at least one protein that co-stimulates T cell activation.

As used herein, the term "at least one protein that co-stimulates T cell activation" refers to the co-stimulatory proteins present on the surface of passenger leukocytes that provide a co-stimulatory signal to activate T lymphocytes. The at least one protein may be selected from: CD40, CD80 or CD86.

The agent may comprise at least one biological molecule and/or chemical compound that has the ability to reduce or inhibit the expression or activity of at least one protein on the surface of passenger leukocytes that co-stimulates T cell activation.

Different biological molecules and/or chemical compounds may be used in combination to treat the isolated passenger leukocytes.

Agents that reduce or inhibit the activity of the at least one protein having co-stimulatory activity may include antagonistic antibodies or antigen-binding fragments thereof that specifically bind to the at least one protein.

As used herein, the term 'antibody' encompasses any polypeptide that comprises an antigen-binding domain. Examples include, but are not limited to, polyclonal, monoclonal, specific, monospecific, polyspecific, humanized, human, single chain, chimeric, synthetic, recombinant, hybrid, mutated, grafted, and in vitro generated antibodies.

As used herein, the term "antigen-binding antibody fragment" includes Fab, F(ab')2, Fv, scFv, Fd, dAb, and other antibody fragments that retain antigen binding function.

As used herein, the term "antagonistic" means that the antibodies or antigen-binding fragments thereof block, inhibit, neutralise or reduce the activity of the protein to which they specifically bind.

In one embodiment, the agent comprises at least one antagonistic antibody or an antigen-binding fragment thereof that binds specifically to at least one protein on the surface of passenger leukocytes that co-stimulates T cell activation.

In one embodiment, the agent comprises at least one antigen-binding antibody fragment that binds specifically to at least one protein on the surface of passenger leukocytes that co-stimulates T cell activation.

In one embodiment, agent comprises at least one Fab fragment that binds specifically to at least one protein on the surface of passenger leukocytes that co-stimulates T cell activation.

In one embodiment, the agent comprises at least one antagonistic antibody or an antigen-binding fragment thereof that binds specifically to at least one protein selected from: CD40, CD80 and CD86.

In one embodiment, the agent comprises at least one antagonistic antibody or antigen-binding fragment thereof that binds specifically to two or more proteins selected from: CD40, CD80 and/or CD86. In one embodiment, the antagonistic antibody is a bispecific antibody that binds specifically to two or more proteins selected from: CD40, CD80 and/or CD86.

In one embodiment, the agent comprises a combination of at least two antagonistic antibodies or antigen-binding fragments thereof that bind specifically to at least two proteins selected from: CD40, CD80 and/or CD80. In one embodiment, the agent comprises a combination of at least two antagonistic antibodies or antigen-binding fragments thereof that bind specifically CD40 and CD80. In one embodiment, the agent comprises a combination of at least two antagonistic antibodies or antigen-binding fragments thereof that bind specifically CD40 and CD86. In one embodiment, the agent comprises a combination of at least two antagonistic antibodies or antigen-binding fragments thereof that bind specifically CD80 and CD86. In one embodiment, the agent comprises a combination of at least two antagonistic antibodies or antigen-binding fragments thereof that bind specifically CD40, CD80 and CD86.

In one embodiment, the agent comprises at least one Fab fragment derived from the anti-CD40 monoclonal antibody produced by the 3A8 hybridoma (ATCC HB-12024; CMCC #11066).

For certain tissues and organs, the antigen-binding fragments may prove particularly useful when passenger leukocytes are treated in situ in the warm perfusion system. For example, when the donor organ is a kidney, intact antibodies are too large to cross the glomerular membrane and smaller antigen-binding fragments are required in order to penetrate the kidney parenchyma to efficiently treat the passenger leukocytes.

Agents that reduce or inhibit protein activity may also include chemical compounds that antagonise, block, inhibit, neutralise or reduce the activity of the protein having co-stimulatory activity.

Agents that reduce or inhibit the expression of the at least one protein having co-stimulatory activity may include antisense oligonucleotides (such as siRNA molecules) which reduce or inhibit the expression of the gene or mRNA sequence encoding the protein. In one embodiment, the agent is at least one antisense oligonucleotide that reduces or inhibits the expression of at least one gene encoding a protein selected from: CD40, CD80 and CD86.

Agents that reduce or inhibit the activity or expression of the at least one protein having co-stimulatory activity may include vectors for gene transfection. In one embodiment, the gene transfection vectors may permit transfection of a gene into the passenger leukocytes that blocks the activity or expression of CD40, CD80 and/or CD86.

The treating step may include incubating the isolated passenger leukocytes with the agent for a time period that is sufficient for the agent to reduce or inhibit the activity of a protein located on the surface of the passenger leukocytes that co-stimulates T cell activation.

The agent may 'reduce' the activity of the co-stimulatory protein by at least 20%, at least 30%, at least 40%, at least 50%, at least 60%, at least 70%, at least 80%, at least 90%, at least 95%, at least 98% or by 100%.

The treatment step may include incubating the isolated passenger leukocytes with the agent for a time period that is sufficient for the agent to reduce or inhibit the expression of a protein located on the surface of the passenger leukocytes that co-stimulates T cell activation.

The agent may 'reduce' the expression of the co-stimulatory protein by at least 20%, at least 30%, at least 40%, at least 50%, at least 60%, at least 70%, at least 80%, at least 90%, at least 95%, at least 98% or by 100%.

As used herein, the term "reintroducing the treated passenger leukocytes into the perfusion solution" refers to the step in which the treated passenger leukocytes are added to the perfusion solution to circulate in the warm perfusion system. The tissue or organ is perfused for a time sufficient for the treated leukocytes to enter the tissue or organ. This means that the tissue or organ is perfused for a duration sufficient to ensure that the treated leukocytes to remain within the tissue or organ.

The step of perfusing the tissue or organ following re-introduction of the treated leukocytes may be performed for at least 1 hour. Alternatively, the perfusion step may be performed for at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 hours. In one embodiment, the perfusion step is performed for at least 24 hours. The step of perfusing the tissue or organ following re-introduction of the treated leukocytes may be performed for up to 36, 48, 72, 96, 120, 144, 168, 192, 216 and 240 hours. In one embodiment, the perfusion step is performed for up to 36 hours.

The step of perfusing the tissue or organ following re-introduction of the treated leukocytes is performed at a temperature of between 25° C. and 37° C. Alternatively, this step may be performed at a temperature between about 25° C. and 35° C. Alternatively, this step may be performed at a temperature between about 30° C. and 34° C. Alternatively, this step may be performed at a temperature of about 32° C.

As used herein, the term "patient" refers to the recipient of a tissue or organ transplant. Typical patients include mammals such as human, primates, and other non-human mammals such as cows, sheep, horses, dogs and cats. In one embodiment, the patient is a human.

As used herein, the phrases "administered directly to the recipient patient" and "administering the treated passenger leukocytes to the recipient patient of the donor tissue or organ" refers to the step in which the treated donor passenger leukocytes are administered to the patient who is going to receive or has received the tissue or organ from which the passenger leukocytes were isolated. The donor passenger leukocytes are therefore autologous to the donor tissue or organ.

The treated passenger leukocytes may be administered to the patient prior to transplantation of the donor tissue or organ. Alternatively, the treated passenger leukocytes may be administered to the patient during transplantation of the donor tissue or organ. Alternatively, the treated passenger leukocytes may be administered to the patient following transplantation of the donor tissue or organ. In one embodiment, the treated passenger leukocytes may be administered to the patient at multiple stages of the transplant process, such as before and during transplantation; before and after transplantation; or during and after transplantation of the donor tissue or organ.

In one embodiment, the treated passenger leukocytes may be administered systemically to the patient prior, during and/or after transplantation of the donor tissue or organ. In one embodiment, the treated passenger leukocytes may be administered systemically to the patient at multiple stages of the transplant process, such as before and during transplantation; before and after transplantation; or during and after transplantation of the donor tissue or organ.

In one embodiment, the treated passenger leukocytes may be administered directly into the transplanted tissue or organ during the transplantation procedure or after transplantation has taken place.

In one embodiment, the treated passenger leukocytes are administered directly to donor tissue or organ prior to transplantation, whilst the tissue or organ is being perfused in a warm perfusion system (as described herein).

In the methods and uses of the invention described herein, the step of establishing the tissue or organ in a warm perfusion system capable of supporting oxidative metabolism of the tissue or organ is performed at a temperature of between 25° C. and 37° C. In one embodiment, the establishing step is performed at a temperature of about 32° C. Alternatively, the establishing step may be performed at a temperature as described above.

In the methods and uses of the invention described herein, the step of perfusing the tissue or organ with a warm non-blood perfusion solution is performed at a temperature of between 25° C. and 37° C. In one embodiment, the perfusion step is performed at a temperature of about 32° C. Alternatively, the perfusion step may be performed at a temperature as described above.

In the methods and uses of the invention described herein, the step of perfusing the tissue or organ with a warm non-blood perfusion solution is performed for at least 1 hour. In one embodiment, the perfusion step is performed for at least 24 hours. Alternatively, the perfusion step may be performed for a minimum time period as described above.

In the methods and uses of the invention described herein, the step of perfusing the tissue or organ with a warm non-blood perfusion solution is performed for up to 36 hours. In one embodiment, the perfusion step is performed for up to 72 hours. Alternatively, the perfusion step may be performed for a maximum time period as described above.

These embodiments of the perfusion step apply equally to the step of perfusing a donor tissue or organ with a perfusion solution that comprises an agent that reduces or inhibits the expression or activity of at least one protein on the surface of passenger leukocytes that co-stimulates T cell activation.

In the methods and uses of the invention described herein, the passenger leukocytes are isolated from the recirculating perfusion solution using filtration. In one embodiment, the filtration may be performed using a porous filter membrane having a pore size that is sufficient to isolate passenger leukocytes from the recirculating perfusion solution, such as a pore size between about 1 µm to about 10 µm. In one embodiment, the filter membrane has a pore size of about 5 µm. Alternatively, the pore size of the filter membrane is as described above.

In the methods and uses of the invention described herein, the agent is at least one biological molecule and/or chemical compound that has the ability to reduce or inhibit the expression or activity of at least one protein on the surface of passenger leukocytes that co-stimulates T cell activation. In one embodiment, the agent is at least one antagonistic antibody or antigen-binding fragment thereof that reduces or inhibits the activity of at least one protein on the surface of the passenger leukocyte that co-stimulates T cell activation. In one embodiment, the agent is least one antisense oligonucleotide that reduces or inhibits the expression of at least one protein on the surface of the passenger leukocyte that co-stimulates T cell activation. In one embodiment, the agent is the anti-CD40 monoclonal antibody produced by the 3A8 hybridoma (ATCC HB-12024; CMCC #11066). Alternatively, the agent may be as described above.

In the methods and uses of the invention described herein, the at least one protein on the surface of the passenger leukocytes that co-stimulates T cell activation is selected from the group consisting of: CD40, CD80 and CD86.

In the methods and uses of the invention described herein, the step of re-introducing the treated passenger leukocytes into the perfusion solution and perfusing the tissue or organ is performed at a temperature of between 25° C. and 37° C. In one embodiment, the perfusion step is performed at a temperature of about 32° C. Alternatively, the perfusion step performed after the treated passenger leukocytes are re-introduced into the perfusion solution may be performed at a temperature as described above.

In the methods and uses of the invention described herein, the step of re-introducing the treated passenger leukocytes into the perfusion solution and perfusing the tissue or organ is performed for at least 1 hour. In one embodiment, the perfusion step is performed for at least 24 hours. Alternatively, the perfusion step performed after the treated passenger leukocytes are re-introduced into the perfusion solution may be performed for a minimum time period as described above.

In the methods and uses of the invention described herein, the step of re-introducing the treated passenger leukocytes into the perfusion solution and perfusing the tissue or organ is performed for up to 36 hours. In one embodiment, the perfusion step is performed for up to 72 hours. Alternatively, the perfusion step performed after the treated passenger leukocytes are re-introduced into the perfusion solution may be performed for a maximum time period as described above.

In the methods and uses of the invention described herein, the perfusion solution comprises a buffered basal medium, essential amino acids, non-essential amino acids, chemical energy substrates, growth factors, and vasodilators. In one embodiment, the perfusion solution comprises a buffered basal medium, essential amino acids, non-essential amino acids, chemical energy substrates, growth factors, and vasodilators and the following specific supplements: pyruvate, glucose, ATP, AMP, coenzyme A, flavin adenine dinucleotide (FAD), thiamine pyrophosphate chloride (cocarboxylase), β-nicotinamide adenine dinucleotide (NAD), β-nicotinamide adenine dinucleotide phosphate (NADP), uridine 5'triphosphate (UTP). In one embodiment, the perfusion solution comprises a buffered basal medium, essential amino acids, non-essential amino acids, chemical energy substrates, growth factors, and vasodilators and the following specific supplements: glucose, ribose, deoxyribose, glutamine, glycine, aspartate, adenosine, adenine, adenosine 5'triphosphate and adenosine 5'monophosphate. Alternatively, the perfusion solution may as described above.

In the methods and uses of the invention described herein, the organ is a kidney.

The present invention is discussed in more detail by means of the Examples described below, and by the Figures.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION OF THE INVENTION

Examples

Figure 1A:
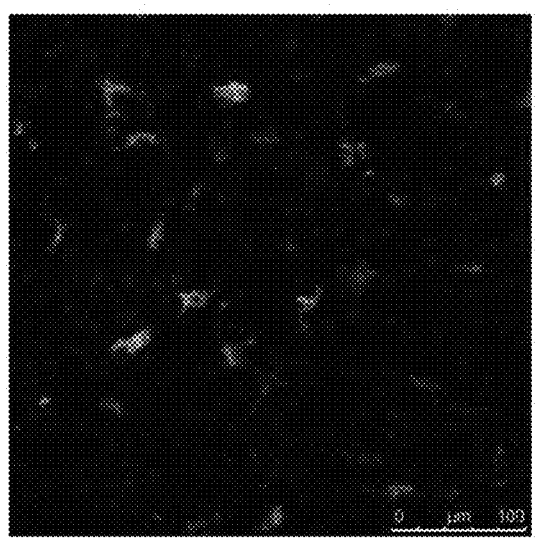
FIGS. 1A and 1B show histologic evaluations of kidney biopsies taken prior to initiating the warm perfusion (FIG. 1A) compared to those following 24 hours of ex vivo warm perfusion (FIG. 1B) as described in Example 1, and demonstrate the removal of passenger leukocytes from the various compartments within the nephron.
Figure 1B:
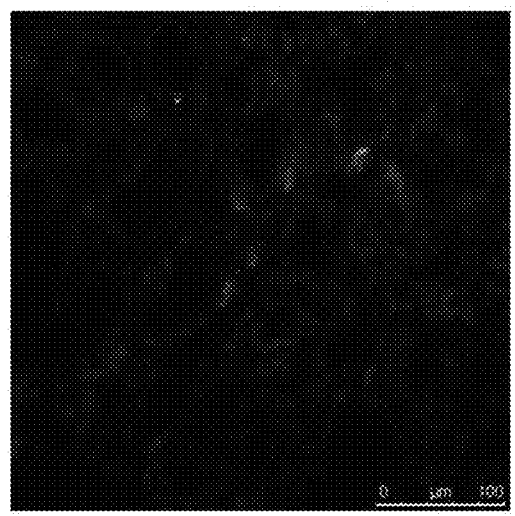

Example 1: Passenger Leukocyte (PL) Determination In Situ

This Example evaluates the potential of reducing immunogenicity of human renal allografts by eliminating the trapped passenger leukocytes.

Human Kidneys:

Human kidneys (n=46) from cadaveric heartbeating donors were procured for transplantation but later became available for research based upon standard institutional criteria. All the kidneys were received on static storage, although 34 of the kidneys (74%) had been hypothermically machine pumped prior to shipment. The other 12 kidneys were simply statically stored without hypothermic perfusion.

The kidneys were weighed, biopsied, cannulated and the vasculature flushed of cold preservation solution. All 46 of the kidneys were re-warmed by flushing with warm (32° C.) solution prior to initiating warm perfusion. All 46 of the kidneys were then established in a warm perfusion system as detailed below.

Warm Perfusion:

We used an acellular Exsanguinous Metabolic Support (EMS) perfusion system to perfuse the kidneys at a temperature of 32° C. for 24 hours. The warm perfusion is required in order to efficiently support continued oxidative metabolism and the resulting synthetic functions. Unlike a traditional bioreactor designed to expand populations of cells isolated by dissociative procedures, the warm perfusion must deliver all of the required molecules to maintain metabolism in the approximately 3-trillion heterogeneous cells that constitute a kidney. Physiologic parameters such as temperature, pH, $O_2$-tension and perfusion pressures were kept within a narrow range to support optimized ex vivo oxidative metabolism. The temperature used was 32° C. The pH range was 7.32-7.37. Oxygen tension ranged from 240-280 mmHg.

The resuscitated metabolism in all of the 46 human kidneys remained stable throughout the 24 hours of ex vivo perfusion. In all cases the oxygen consumption was >0.12 cc/min/g, mean arterial pressure ranged from 40 to 45 mmHg and the vascular flow rate was >1500 cc/minute. Also, in all cases there was evidence of resumed synthetic functions as determined by the presence of synthesis of cytokines and chemokines released into the recirculating perfusate as determined using the luminex platform.

The perfusion solution used in the experiment was based on the solution disclosed in Table 2 of the application, supplemented with the reagents required to support ATP synthesis including glucose at a concentration of 2 g/L; ribose at a concentration of 10 mg/L; deoxyribose at a concentration of 10 mg/L; glutamine at a concentration of 200 mg/L; glycine at a concentration of 100 mg/L; aspartate at a concentration of 120 mg/L; adenosine at a concentration of 4 mg/L; adenine at a concentration of 20 mg/L adenosine 5'triphosphate at a concentration of 38 mg/L; and adenosine 5'monophosphate at a concentration of 4 mg/L.

The EMS perfusion technology is based upon tissue culture principles that incorporate dynamic oxidative/reduction functions involving individual perfusate components that are interactive in order to support adequate basal metabolism. Similarly, the vascular function as a refined charge barrier is preserved.

Analysis of Renal Allograft Biopsies

The passenger leukocyte population trapped within renal allografts from 46 human kidney donors was evaluated in terms of density, phenotype and migratory functions during 24-hours of ex vivo warm perfusion.

Biopsies were taken pre- and post-warm perfusion (24 hours). Frozen sections were made from ten representative sections within each kidney. For the purpose of this study the number and location of passenger leukocytes within the kidneys were determined using an indirect immunofluorescence assay utilizing a mouse Anti-DC-SIGN (ABCAM) (also synonymous with CD209), that is specific for macrophages and dendritic cells. The tissue sections were then mounted using Fluoroshield+DAPI. The total white blood cell population of PL was determined using a mouse anti-11c antibody with the same indirect immunofluorescence assay. The results were quantified using ImageJ software measuring positive fluorescence per field within each of the ten representative sections from each human kidney.

Figure 2A:
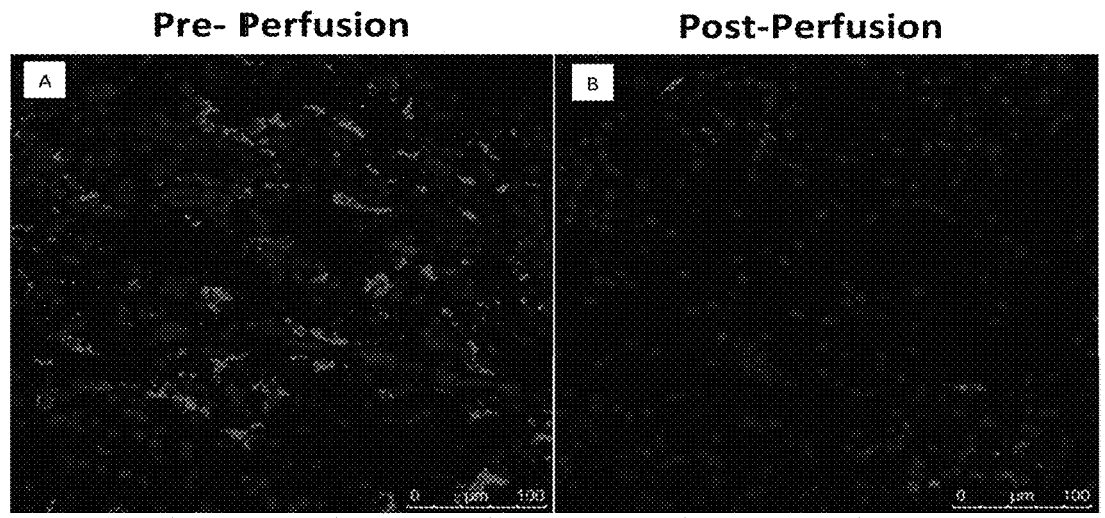
FIGS. 2A and 2B also show histologic evaluations of kidney biopsies taken prior to initiating the warm perfusion (left panel) compared to those following 24 hours of ex vivo warm perfusion (right panel). Tissue is stained with an anti-DC-SIGN antibody and with DAPI.
Figure 2B:
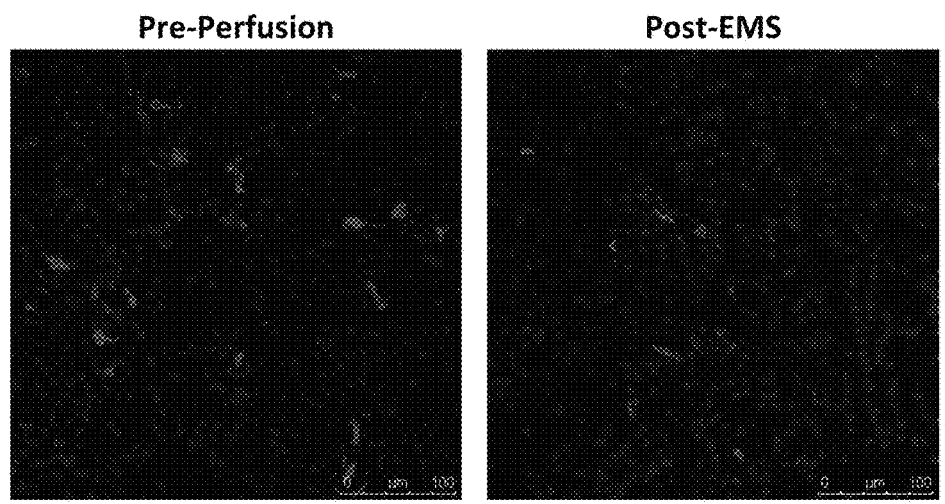
Figure 3:
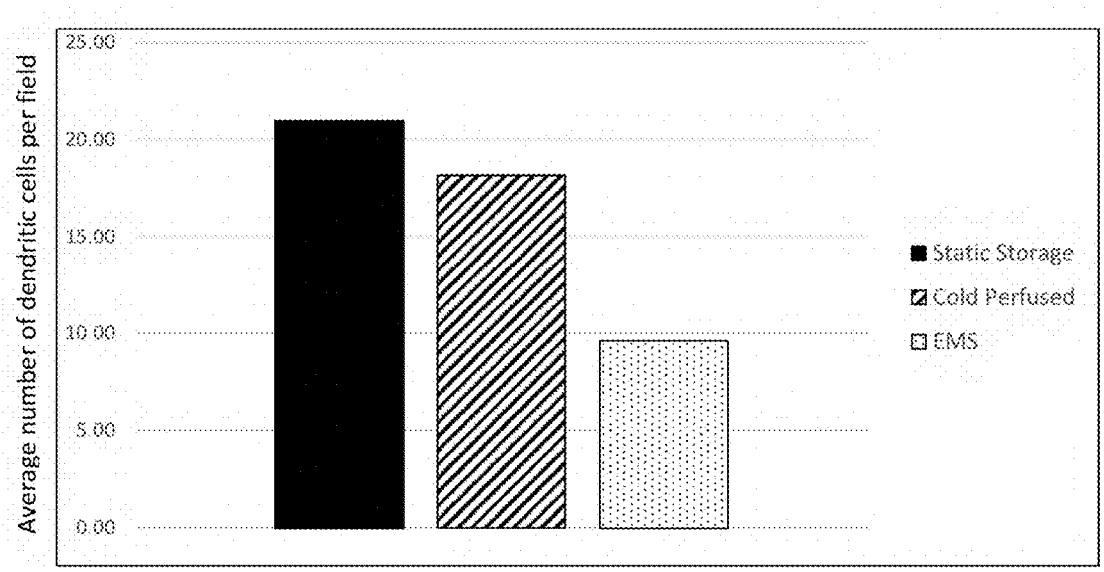
FIG. 3 illustrates that migration of dendritic cells out of allografts is temperature dependent, and plots the average number of dendritic cells remaining within kidneys following static storage, cold perfusion, and warm (EMS) perfusion (as described in Example 3). Warm (EMS) perfused kidneys had a significantly lower average number of positive stained cells per field compared to static storage or cold perfused kidneys (p<0.05).

Histologic evaluations of biopsies taken prior to initiating the warm perfusion compared to those following 24 hours of ex vivo warm perfusion demonstrated the removal of the passenger leukocytes from the various compartments within the nephron. Representative tissue staining for the kidney biopsies taken pre-perfusion and 24 hours post perfusion are shown in FIGS. 2 & 3. The fluorescent signal observed correlates with the presence of passenger leukocytes within the allograft. The total number of cells staining positive for DC-SIGN (or CD209) decreased in the biopsies taken 24 hours post EMS perfusion as compared to the pre-perfusion biopsies.

The results of the histologic evaluations are also expressed as the mean cell-count/60 fields in Table 1 shown below. Histologic evaluations supported the removal of passenger leukocytes from the various compartments within the nephron when the pre-perfusion biopsy was compared to those following 24 hours of ex vivo warm perfusion. A significant reduction in the number of resident passenger leukocytes was observed within the various compartments of the kidneys following approximately 24 hours of EMS perfusion.

In addition to analyzing the kidney biopsies, the recirculating perfusion solution was also analysed for the presence of passenger leukocytes. Following 24 hours of EMS perfusion, the recirculating perfusion solution was collected and the volume was centrifuged to collect any cells that had migrated out from the kidney in the circulation. Using an in-line cell processor, the recirculating perfusate effluent leaving the renal artery is passed through the processor containing a membrane with a pore size that prevents any cells migrating from the renal parenchyma to continue circulating in the perfusate. The transmembrane pressure is maintained by the perfusion system's circulating mean pressures and its associated vascular flow rates. The passenger leukocytes that remain in the upper chamber of the cell processor can be removed via a port perpendicular to the direction of the perfusate flow through the device by aspiration with a syringe.

Since the EMS solution is acellular, any cells found in the perfusion solution originated from the kidney itself. The pelleted cells were resuspended and their concentrations were determined by counting with a hemocytometer. The phenotype of the passenger leukocytes collected from the perfusion solution was determined by indirect immunofluorescence staining with the CD209 antibody as described above. The total number of passenger leukocytes observed in the perfusate following 24 hours of warm perfusion is shown in Table 3.

An increasing concentration of passenger leukocytes is found in the circulating EMS solution after perfusion. An additional consideration is that since the migrating passenger leukocytes were not trapped and removed from the recirculating perfusion solution, re-entry into the kidney was not prevented. Therefore, the number of passenger leukocytes migrating into the EMS solution may be underestimated in this study.

TABLE 3

Elimination of DC+ in Human Kidneys during EMS Perfusion□†

|  | Pre-EMS Perfusion | Post-EMS Perfusion |
| --- | --- | --- |
| Kidney DC-sign * | 12.78 ± 9.1 | 6.06 ± 3.67 |
| Perfusate DC† | 0 | $3.02 \times 10^6$ |

□Kidney DC-sign: mean/60 field
†Conc. of DC is circulating perfusate

Example 2: PL Migration Determinations

When performing the warm perfusion study of Example 1, samples of recirculating perfusion solution were collected at various time points to investigate the migration of passenger leukocytes from the kidney throughout the 24 hour perfusion step.

Samples of recirculating perfusion solution were collected at 6, 14 and 24 hours from the warm perfusion system. The recirculating perfusion solution was collected and centrifuged to collect any cells that had migrated out from the kidney into the circulation. Since the perfusate solution is acellular, any cells found in the perfusion solution originated from the kidney itself. The total pelleted cell population was resuspended and the concentrations were determined by cell counting. The phenotypes of the passenger leukocytes collected from the perfusion solution was determined by indirect immunofluorescence staining with a panel of antibodies by flow cytometry, as described in Example 1.

The number of passenger leukocytes migrating out of the renal parenchyma into the perfusate is shown in Table 4. The results demonstrate that passenger leukocyte migration out of the renal parenchyma is time dependent and that longer ex vivo perfusion times are requisite to maximizing the recovery of the intrarenal PL.

TABLE 4

| Migration over time | | | |
| --- | --- | --- | --- |
| Perfusion time | 6 hours | 14 hours | 24 hours |
| Passenger Leukoyte Count | $9.5 \times 10^6$ (±2.1) | $16.9 \times 10^6$ (±1.9) | $21.7 \times 10^6$ (±2.4) |

Example 3: Lack of PL Migration in Hypothermically Preserved Allografts

To investigate the effect of performing the ex vivo perfusion step at a physiologic (warm) temperature, a study was performed to compare the numbers of passenger leukocytes trapped within the kidneys when using (i) warm perfusion; (ii) hypothermic perfusion; and (iii) no perfusion (ie. static preservation).

Figure 4:
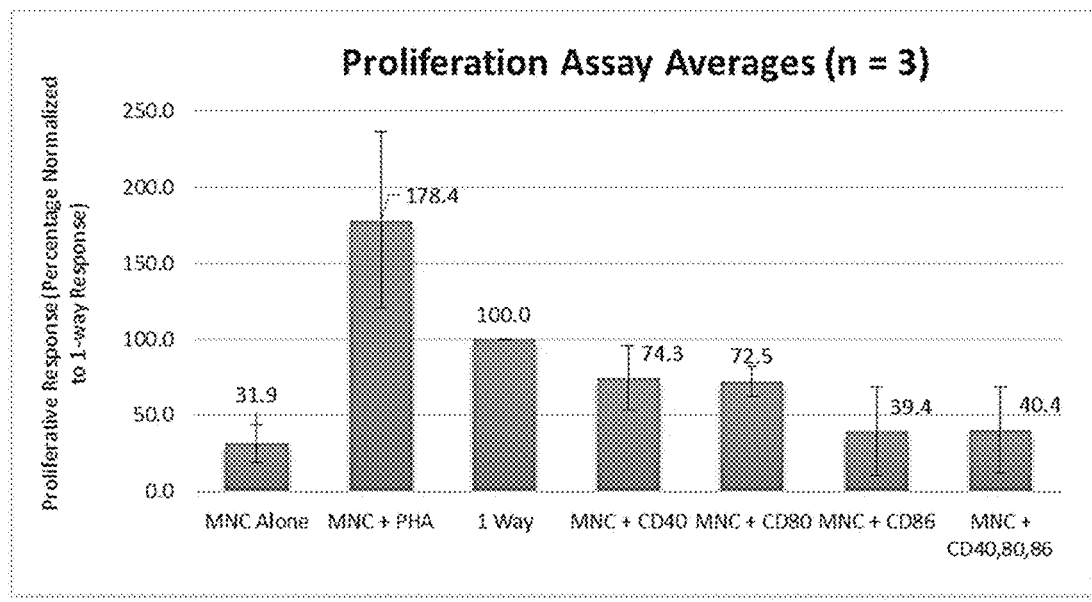
FIG. 4 illustrates the proliferative response of passenger leukocytes recovered from kidneys when treated with antagonist antibodies (as described in Example 4). "MNC Alone"=mononuclear cells without stimulator allogeneic cells. "MNC+PHA"=mononuclear cells stimulated with phytohemagglutatinin (positive control). "1 Way"=MNC+ untreated stimulator allogeneic cells. Results were normalized against the "1 Way" proliferative reaction.

Paired kidneys were used in the investigation. One half of kidney pair was warm perfused (n=8), whilst the other was either hypothermically at 4° C. perfused (n=5) or preserved statically (n=3). Using the method described above for Example 1, the number of passenger leukocytes trapped within the kidneys was investigated after 24 hours of perfusion or static preservation. The results are shown in FIG. 4.

In the statically stored kidneys the mean population of passenger leukocytes was approximately 21 (+/−16.4) cells per field. In the kidneys that were hypothermically perfused, the mean population of passenger leukocytes was approximately 19 (+/−6.8) cells per field. The population of passenger leukocytes in the hypothermically perfused kidneys is therefore very similar to the population observed in the kidneys that were preserved statically (the small difference observed in population size is not statistically significant). In contrast, in the warm perfused kidneys the population of passenger leukocytes was significantly reduced with a mean of 9.8 (+/−8.0) cells per field (p<0.05).

These results confirm that when the kidney is perfused in a warm perfusion system, the passenger leukocytes are able to freely migrate in and out of the renal parenchyma. In contrast, when hypothermic perfusion is used or static preservation, the passenger leukocytes do not readily migrate out from the renal parenchyma but rather remain trapped within the kidneys. The trapping of the passenger leukocytes within the parenchyma of hypothermically perfused or statically preserved kidneys negates the possibility of treating or removing them prior to transplantation.

These results confirm that incubating a tissue or organ at a physiological temperature, encourages cellular metabolism and the generation of ATP energy resources required for migration of the passenger leukocytes. In contrast, when hypothermic perfusion is performed, oxidative metabolism is inhibited, and ATP and ADP stores become depleted. There is also a generalized inhibition of the ion pumps that results in cellular swelling; and inactivation of the mitochondrial transport enzymes.

Example 4: Costimulatory Blockade

Since activation of T cells without costimulation may lead to T cell anergy, we evaluated whether the passenger leukocytes from the kidneys could be treated with antibodies to interfere with costimulation. Responding mononuclear cells were isolated from peripheral blood using Ficoll-Hypaque gradients. The passenger leukocytes from the human kidneys were treated with antagonist antibodies to CD40, CD80, CD86 and with various combinations of the three antibodies. LEAF™ Antibodies (low endotoxin, azide free) antibodies were prepared and purified using affinity chromatography. A concentration of 5 µg/ml was used in attempt to block a proliferative response. The treated passenger leukocytes were then used as the stimulatory cells in a standard bromodeoxyuridine (BrdU) proliferation assay and analyzed using a Victor$^2$ Multiwell Plate Reader.

Negative controls in the experiment included a sample of mononuclear cells alone (MNC alone), and mononuclear cells incubated with untreated stimulator allogeneic cells (1 way). Results were normalized using the "1 way" proliferative control.

A positive control was included in the experiment as mononuclear cells stimulated with phytohemagglutatinin (MNC+PHA).

Figure 5:
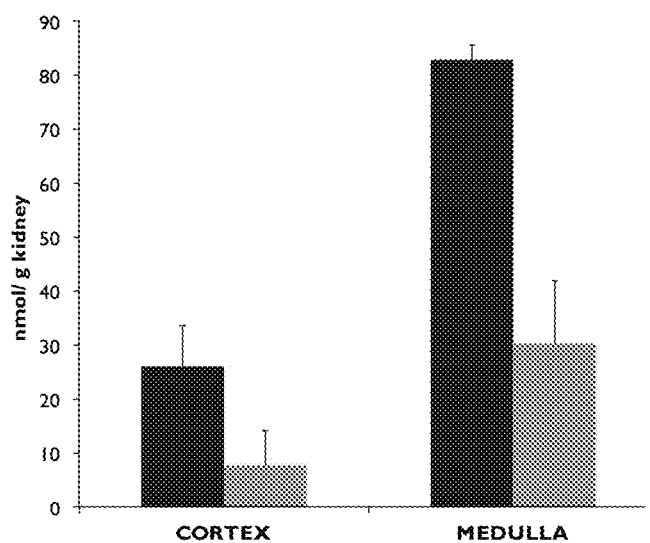
FIG. 5 illustrates the increased level of ATP generated in the cortex and medulla of a kidney during warm perfusion when the perfusion solution is supplemented with key intermediates in the ATP synthesis pathway (as described in Example 6). As a control, a kidney was also incubated in the perfusion system using a perfusion solution without added ATP intermediate supplements.
Figure 6:
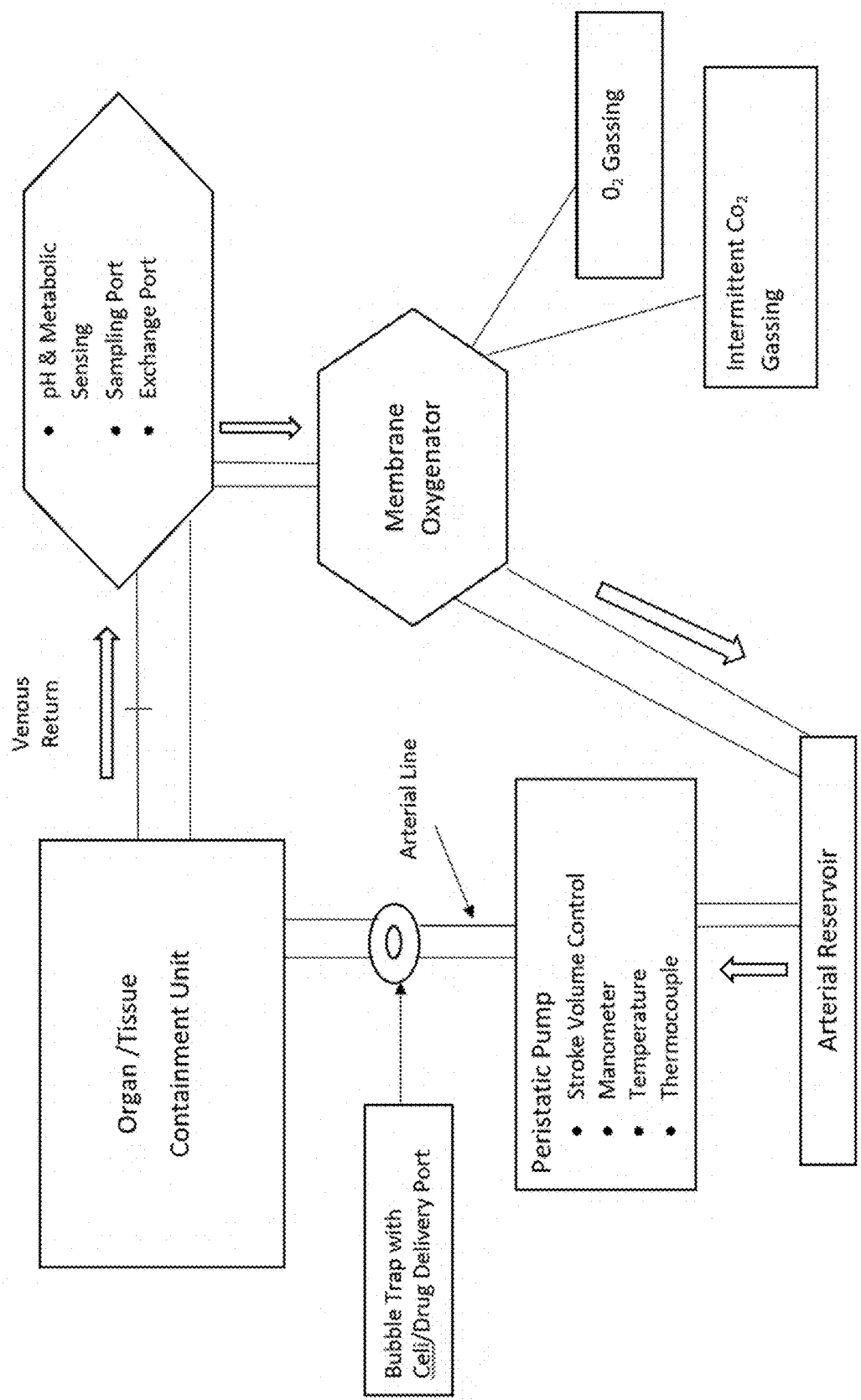
FIG. 6 is a schematic of the warm (EMS) perfusion system used in the methods and uses of the invention. A full description of this system is provided in WO 2004/105484.

Treating the recovered passenger leukocytes with the different antibodies resulted in blockade of a proliferative response (FIG. 5). The greatest costimulatory blockade was observed with the single treatment of anti-CD86 that mediated 89% inhibition of the proliferative response. Treatment with anti-CD40 and anti-CD80 alone did not totally block the proliferative response; although combined treatment of both antibodies did effectively prevent the proliferation. The combined treatment of anti-CD40, anti-CD80 and anti-CD86 also resulted in inhibition of the proliferative response. These results demonstrate the potential for effective costimulatory blockade by treating donor passenger leukocytes recoverable following ex vivo warm perfusion.

Example 5: Treatment of the Whole Allograft

The costimulatory blockade can also be accomplished by administering the desired therapeutic to the whole allograft. The costimulatory blockade studies were repeated administering anti-CD86 antibody directly to human kidneys via the renal artery during the 24-hour period of warm perfusion. Vascular endothelial cells were isolated from the human kidneys by perfusing the vasculature with a 1% collagenase solution after the PL cells had been collected from the perfusate. Both cell types were used in proliferation assays as described above in Example 4. T cell proliferation was equivalently prevented by treating the PL or alternatively the vascular endothelial cells isolated from the human kidneys. Therefore achieving costimulatory blockade using either PL or vascular endothelial cells prevented both direct and indirect antigen presentation.

Example 6: ATP Synthesis

A study was performed to investigate whether supplementing the perfusion solution with factors that promote ATP synthesis can help to increase the availability of energy resources needed for migration of passenger leukocytes.

Migration of passenger leukocytes out of donor tissues and organs is dependent on (i) the temperature at which perfusion is performed (temperatures in the range of 25° C. to 37° C. support oxidative metabolism); and (ii) the availability of intracellular energy stores.

Kidneys (n=10) contained within a warm perfusion system were provided with a warm perfusion solution containing factors for ATP synthesis; including glucose (an integral starting substrate), ribose and deoxyribose (intermediates that are involved in the formation inosine monophosphate), glutamine, glycine and aspartate (also required for formation of inosine monophosphate), and adensine, adenine, adenosine 5'triphosphate and adenosine 5'monophosphate (which further support ATP synthesis).

In particular, the perfusion solution was prepared with glucose at a concentration of 2 g/L; ribose at a concentration of 10 mg/L and deoxyribose at a concentration of 10 mg/L; glutamine at a concentration of 200 mg/L; glycine at a concentration of 100 mg/L; aspartate at a concentration of 120 mg/L; adenosine at a concentration of 4 mg/L; adenine at a concentration of 20 mg/L, adenosine 5'triphosphate at a concentration of 38 mg/L and adenosine 5'monophosphate at a concentration of 4 mg/L.

Results from the study are shown in FIG. 5. A comparison was made between kidneys perfused using a perfusion solution containing the additional substrates; and those perfused using a perfusion solution that does not contain the specified ATP synthesis substrates.

A significant increase in ATP levels was observed in the cortex and medulla of the kidneys perfused using the solution containing the additional substrates.

The invention claimed is:

1. An ex vivo method for reducing the immunogenicity of a tissue or organ prior to transplantation, comprising:
    (a) establishing the tissue or organ in a perfusion system to support oxidative metabolism of the tissue or organ;
    (b) perfusing the tissue or organ with a non-blood perfusion solution for at least 1 hour to allow passenger leukocytes within the tissue or organ to migrate from the tissue or organ into the recirculating perfusion solution;
    (c) isolating the passenger leukocytes from the recirculating perfusion solution to prevent the passenger leukocytes from re-entering the tissue or organ;
    (d) treating the isolated passenger leukocytes with an agent that reduces or inhibits the expression or activity of at least one selected from the group consisting of CD40, CD80 and CD86 on the surface of the passenger leukocyte; and
    (e) re-introducing the treated passenger leukocytes into the tissue or organ by adding the treated passenger leukocytes to the perfusion solution and perfusing the tissue or organ for a time sufficient for the treated leukocytes to enter the tissue or organ, wherein the step (a) and/or (b) is performed at a temperature of between 25° C. and 37° C.

2. An ex vivo method according to claim 1, wherein step (b) is performed for at least 24 hours.

3. An ex vivo method of claim 1, wherein the passenger leukocytes are isolated from the recirculating perfusion solution by filtration.

4. An ex vivo method according to claim 1, wherein the agent is an antibody or antigen-binding fragment thereof that reduces or inhibits the activity of at least one of CD40, CD80 and/or CD86 on the surface of the passenger leukocyte.

5. An ex vivo method of claim 1, wherein step (e) is performed at a temperature of between 25° C. and 37° C.

6. An ex vivo method of claim 1, wherein step (e) is performed for at least 1 hour.

7. An ex vivo method of claim 1, wherein the organ is a kidney.

* * * * *